(12) United States Patent
Smetters et al.

(10) Patent No.: US 7,937,089 B2
(45) Date of Patent: May 3, 2011

(54) METHOD, APPARATUS, AND PROGRAM PRODUCT FOR PROVISIONING SECURE WIRELESS SENSORS

(75) Inventors: Diana K. Smetters, San Francisco, CA (US); Dirk Balfanz, Menlo Park, CA (US); Glenn E. Durfee, San Francisco, CA (US); Rebecca E. Grinter, San Francisco, CA (US); Paul J. Stewart, Sunnyvale, CA (US); Hao-Chi Wong, San Carlos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 315 days.

(21) Appl. No.: 10/656,551

(22) Filed: Sep. 5, 2003

(65) Prior Publication Data

US 2004/0266449 A1 Dec. 30, 2004

Related U.S. Application Data

(63) Continuation-in-part of application No. 11/395,274, filed on Apr. 3, 2006, which is a continuation of application No. 10/066,699, filed on Feb. 6, 2002.

(60) Provisional application No. 60/480,909, filed on Jun. 24, 2003.

(51) Int. Cl.
*H04W 72/00* (2009.01)
*H04L 9/32* (2006.01)

(52) U.S. Cl. .................. 455/452.1; 455/450; 455/422.1; 713/168; 713/158; 713/163; 713/170; 713/171

(58) Field of Classification Search ............... 455/452.1, 455/452.2, 422.1, 450, 509; 713/186, 187, 713/202, 156, 158, 163, 168, 170, 171, 150; 726/5, 18, 19; 380/282, 285, 277, 207, 278; 340/5.72

See application file for complete search history.

(56) References Cited

U.S. PATENT DOCUMENTS

| 5,341,426 A | 8/1994 | Barney et al. |
| 5,408,250 A | 4/1995 | Bier ............................. 345/169 |
| 5,519,778 A | 5/1996 | Leighton et al. ............... 380/30 |
| 5,539,824 A | 7/1996 | Bjorklund et al. ............. 380/21 |
| 6,061,791 A * | 5/2000 | Moreau ........................ 713/171 |
| 6,064,741 A | 5/2000 | Horn et al. .................... 380/285 |

(Continued)

FOREIGN PATENT DOCUMENTS

EP 1024626 A1 1/1999

(Continued)

OTHER PUBLICATIONS

Balfanz et al. (Talking to Strangers: Authentication in Ad-Hoc Wireless Networks), Mar. 11, 2002.*

(Continued)

*Primary Examiner* — Ajit Patel
*Assistant Examiner* — Khai M Nguyen
(74) *Attorney, Agent, or Firm* — Park, Vaughan, Fleming & Dowler LLP; Shun Yao

(57) ABSTRACT

We present technology that allows layman computer users to simply create, provision, and maintain secured infrastructure—an instant PKI. This technology can be used in a wide variety of applications including wired and wireless networks, secure sensor networks (such as medical networks), emergency alert networks, as well as simply and automatically provisioning network devices whether secure or not.

19 Claims, 12 Drawing Sheets

U.S. PATENT DOCUMENTS

| | | | |
|---|---|---|---|
| 6,075,860 A | 6/2000 | Ketcham | 380/25 |
| 6,105,133 A | 8/2000 | Fielder et al. | 713/169 |
| 6,243,373 B1 | 6/2001 | Turock | 370/352 |
| 6,243,772 B1 | 6/2001 | Ghori et al. | 710/68 |
| 6,366,654 B1 | 4/2002 | Cramer et al. | 379/93.09 |
| 6,873,853 B2* | 3/2005 | Kim | 455/466 |
| 7,027,836 B2 | 4/2006 | Zacks et al. | |
| 7,110,982 B2* | 9/2006 | Feldman et al. | 705/51 |
| 7,275,156 B2* | 9/2007 | Balfanz et al. | 713/168 |
| 2001/0029535 A1* | 10/2001 | Hirano et al. | 709/224 |
| 2001/0048744 A1 | 12/2001 | Kimura | 380/247 |
| 2002/0022483 A1 | 2/2002 | Thompson et al. | |
| 2002/0061748 A1 | 5/2002 | Nakakita et al. | 455/435 |
| 2002/0065065 A1 | 5/2002 | Lunsford et al. | 455/411 |
| 2002/0094087 A1 | 7/2002 | Dellmo et al. | 380/270 |
| 2002/0147920 A1 | 10/2002 | Mauro | 713/200 |
| 2002/0159598 A1 | 10/2002 | Rubenstein et al. | 380/259 |
| 2002/0174073 A1* | 11/2002 | Nordman et al. | 705/64 |
| 2002/0176579 A1 | 11/2002 | Deshpande et al. | |
| 2002/0188848 A1* | 12/2002 | Buttiker | 713/175 |
| 2003/0014646 A1 | 1/2003 | Buddhikot et al. | 713/184 |
| 2003/0051140 A1 | 3/2003 | Buddhikot et al. | 713/169 |
| 2003/0078072 A1 | 4/2003 | Serceki et al. | 455/557 |
| 2003/0081774 A1 | 5/2003 | Lin et al. | 380/44 |
| 2003/0095663 A1 | 5/2003 | Nelson et al. | |
| 2003/0117985 A1 | 6/2003 | Fujii et al. | 370/338 |
| 2003/0146847 A1 | 8/2003 | Swetlik et al. | |
| 2003/0158960 A1* | 8/2003 | Engberg | 709/237 |
| 2003/0163686 A1* | 8/2003 | Ward et al. | 713/156 |
| 2003/0212589 A1* | 11/2003 | Kish | 705/9 |
| 2004/0030887 A1 | 2/2004 | Harrisville-Wolff et al. | |
| 2004/0054899 A1* | 3/2004 | Balfanz et al. | 713/168 |
| 2004/0088548 A1 | 5/2004 | Smetters et al. | 713/175 |
| 2004/0098581 A1* | 5/2004 | Balfanz et al. | 713/155 |
| 2004/0103280 A1 | 5/2004 | Balfanz et al. | 713/169 |
| 2004/0215488 A1* | 10/2004 | Hein et al. | 705/2 |
| 2004/0230809 A1* | 11/2004 | Lowensohn et al. | 713/186 |
| 2005/0125669 A1* | 6/2005 | Stewart et al. | 713/171 |
| 2005/0129240 A1* | 6/2005 | Balfanz et al. | 380/270 |
| 2006/0030759 A1* | 2/2006 | Weiner et al. | 600/300 |

FOREIGN PATENT DOCUMENTS

| | | |
|---|---|---|
| EP | 1024626 A1 * | 8/2000 |
| EP | 1335563 A2 | 8/2003 |
| WO | WO 99/41876 | 8/1999 |
| WO | WO-01/17425 A2 | 3/2001 |

OTHER PUBLICATIONS

European Search Report for EP counterpart Application No. 04255294.3, Mar. 21, 2005.

U.S. Appl. No. 10/424,191 entitled "System and Method for Establishing Secondary Channels" to Conley et al.

U.S. Appl. No. 10/656,439 entitled "Method, Apparatus, and Program Product for Securely Presenting Situation Information" to Smetters et al.

Asokan, N. et al.: "Key agreement in ad hoc networks", Computer Communications, Elsevier Science Publishers BV, Amsterdam, NL, vol. 23, No. 17, Nov. 1, 2000, pp. 1627-1637.

Balfanz, D. et al., "Talking to Strangers: Authentication in Ad-Hoc Wireless Networks," Xerox Palo Alto Research Center, [Retrieved from the Internet at http://www.isoc.org/isoc/conferences/ndss/02/proceedings/papers/balfan.pdf on Feb. 18, 2003] (Posted on the Internet on Feb. 11, 2002).

Dridi, F. et al., "How to Implement Web-Based Groupware Systems Based on WebDAV," Published in Proc. of WETICE 99, IEEE 8th Intl. Workshops on Enabling Technologies: Infrastructure for Collaborative Enterprises, Stanford, CA, pp. 1-7 (1999).

Fielding, R. et al., "Web-Based Development of Complex Information Products," Communications of the ACM, vol. 41, No. 8, pp. 84-92 (1998).

Lopes, D. et al., "Aerial Acoustic Communication," IEEE Workshop on Applications of Signal Processing to Audio and Acoustics, pp. 21-24, (2001).

Schneier, Bruce: "Applied Cryptography: Protocols, Algorithms, and Source Code in C" 1996, John Wiley & Sons, New York, US, Section 8.3 "Transferring Keys".

Stajano, F. and Anderson, R.: "The Resurrecting Duckling: Security Issues for Ad-hoc Wireless Networks" 1999, AT&T Software Symposium, 'Online!' Sep. 15, 1999.

Whitehead, Jr., E. et al., "WebDAV, A Network Protocol for Remote Collaborative Authoring on the Web," pp. 1-21 (1999) [Retrieved from the Internet at http://citeseer.nj.nec.com/whitehead99webdav.html on Mar. 11, 2003].

Whitehead, Jr., E. et al., "Lessons from WebDAV for the Next Generation Web Infrastructure," Department of Information and Computer Science, University of California [Retrieved from the Internet at http://www.ics.uci.edu/~ejw/http-future/Whitehead/http_pos_paper.html on Sep. 20, 2002].

Bardram, Jakob E. et al. "Context-Aware User Authentication-Supporting Proximity-Based Login in Pervasive Computing", A.K. Dey et al. (Eds.): UbiComp 2003, LNCS 2864, pp. 107-123, 2003.

Geer, Daniel E. et al. "Token-Mediated Certification and Electronic Commerce", Proceedings of the Second USENIX Workshop on Electronic Commerce, Oakland, California, Nov. 1996.

Kindberg, Tim and Zhang, Kan "Secure Spontaneous Device Association", A.K. Dey et al. (Eds.): UbiComp 2003, LNCS 2864, pp. 124-131, 2003.

Kindberg, Tim and Zhang, Kan "Validating and Securing Spontaneous Associations between Wireless Devices" HP Laboratories, Palo Alto, HPL-2002-256, Hewlett-Packard Company, Sep. 12, 2002.

"ACC: Automatic Cryptographic Configuration of Embedded Devices" XML Trust Center White Paper 19th Feb. 2002, http://research.verisign.com/Papers/ACC1.html.

U.S. Appl. No. 60/480,909 entitled "Methods and Apparatus for Establishing and Using a Secure Credential Infrastructure" to Diana K. Smetters et al., filed Jun. 24, 2003.

U.S. Appl. No. 10/066,699 entitled "Systems and Methods for Authenticating Communications in a Network Medium" to Dirk Balfanz et al., filed Feb. 6, 2002.

U.S. Appl. No. 10/231,194 entitled "Apparatus and Methods for Providing Secured Communication" to Dirk Balfanz et al., filed Aug. 30, 2002.

* cited by examiner

METHOD, APPARATUS, AND PROGRAM PRODUCT FOR PROVISIONING SECURE WIRELESS SENSORS

RELATED APPLICATIONS

This application claims benefit of U.S. Provisional Patent Application 60/480,909 filed 24 Jun. 2003, entitled "Method And Apparatus For Establishing And Using A Secure Credential Infrastructure" with inventors Smetters, Balfanz, Durfee, Grinter, Stewart, Hao-and Wong hereby incorporated by reference in its entirety herein. This application is a continuation-in-part of U.S. patent application Ser. No. 11/395,274 filed 3 Apr. 2006, entitled "Systems and Methods for Authenticating Communications in a Network Medium," which is a continuation of U.S. patent application Ser. No. 10/066,699 filed on 6 Feb. 2002.

This application is related to:

U.S. patent application Ser. No. 10/656,494 entitled "Method. Apparatus, and Program Product for Automatically Provisioning Secure Network Elements" filed concurrently herewith, with the same inventors.

U.S. patent application Ser. No. 10/656,550 entitled "Method and Apparatus for Establishing and Using a Secure Credential Infrastructure" filed concurrently herewith, with the same inventors.

U.S. patent application Ser. No. 10/656,439 entitled "Method. Apparatus, and Program Product for Securely Presenting Situation Information" filed concurrently herewith, with the same inventors.

U.S. patent application Ser. No. 10/066,699 entitled "Systems And Methods For Authenticating Communications In A Network Medium" filed Feb. 6, 2002 with inventors Balfanz, Lopes, Smetters, Stewart, and Wong.

BACKGROUND

1. Field

Embodiments of this invention relate to the field of cryptography.

2. Background

Adoption of public key cryptography has been tremendously limited by the "key management problem"that is, the problem of allowing users to reliably identify the public keys of their intended communication partners. One approach used to address this problem is to construct a Public Key Infrastructure (PKI). This approach designates one or more trusted public keys known by the members of the PKI. The computer system that has the trusted public keys can sign digital certificates containing the public keys of users and devices in the PKI. This process authenticates the public keys of the PKI members.

The primary difficulty addressed by PKI is the problem of key management and distribution. That is, of deciding how to get authenticated copies of particular individuals' or devices' public keys to those individuals and devices that need to rely on these keys. A PKI is a system of well-known trusted public keys, possibly hierarchically organized. In PKI the owner of a trusted key is usually termed a "Certification Authority", or CA. Those trusted keys are used to authenticate the keys of other members (users and devices) in the PKI by signing the keys for the members, thus creating a "digital certificate". Such a certificate typically uses this trusted signature to link a public key to information indicating who owns the key (an identity certificate), or what the key is allowed to be used for (an attribute certificate), or at very minimum, just that the bearer of the corresponding private key is a valid member of this particular PKI or other trust system.

Such a PKI simplifies the key management problem, as the number of keys that must be exchanged a priori goes from many down to the number of the trusted public keys. As long as the information contained in a member's certificate is sufficient to indicate to the verifier of that certificate that they are communicating with their intended party, the signature on that certificate is enough to let them know that the public key contained therein belongs to a trusted entity.

Unfortunately, creation and management of PKIs, as well as distribution of certificates, has turned out to be incredibly difficult and complex. Even establishment of small special-purpose PKIs to support the use of public key cryptography for one application within one organization is generally considered to be too expensive and difficult. One reason for this is that the available software is complicated, expensive, and requires deep knowledge of standards and cryptography to be configured to be effective. As a result, in spite of the fact that the use of public key cryptography can dramatically increase the security of many communications protocols (as compared, for example, to password-based alternatives), protocol designers are forced to move to less secure alternatives that do not require the "burden" of PKI establishment. Similarly, this cost of setting up a PKI keeps individuals from considering larger-scale use of public key cryptography in embedded devices (e.g. cell phones, printers, etc), as each of these devices would have to be "provisioned" with a certificate before use.

Furthermore, the key management and distribution problem described above in the PKI context exists with any secure credential infrastructure that has a credential issuing authority to issue credentials.

A derivative problem exists for wireless networks. These networks have proved notoriously difficult for even knowledgeable corporate IT departments to configure securely. This has led to many deployed networks exposing information and network resources to strangers thus, leaving client machines vulnerable to attack. While standards bodies have begun to specify technologies capable of securing these networks, these new security technologies are complex, and even more difficult to configure and manage than the existing technologies. In many environments (for example home or small business wireless networks), it will be difficult, if not impossible, for network users to effectively configure and manage these networks to make them secure (many current wireless users find that 802.11b WEP is difficult to configure).

The standards body responsible for improving the security of the 802.11 standard are adapting the 802.1x standard for use on 802.11 networks.

In 802.1X's most secure configuration, clients and authentication servers authenticate each other and secure their communications using Transport Layer Security (TLS), which requires both the client and server to have a digital certificate with which they authenticate to each other. To distribute such certificates requires the deployment of a PKI (or other secure credential infrastructure) and the installation of a unique client certificate on each network client. This is a notoriously difficult task and subject to incorrect configurations that can leave clients vulnerable to rogue machines who can gain access to the shared wireless medium; those rogue machines can then use those vulnerable (but authenticated) clients as a base from which to attack the corporate LAN. Again, in situations where this approach is successful, it is either difficult to configure and manage, expensive, or totally out of the reach of small network users.

Similar problems also exist for simple wired networks. For example, if providing static IP addresses or adding a computer to a domain, currently an employee often must have their computer configured by an IT professional responsible for maintaining the addresses.

Another problem exists in the medical field. Security for patient data in the hospital setting has always been important, but with the advent of new HIPAA guidelines, it has become legally mandatory. At the same time, sensors or devices that gather patient data must be highly usable by a community of doctors and nurses who may not be experts in computer technology.

Today, nurses' assistants manually measure and record temperature and blood pressure. These measurements are available through a physical chart, providing no ability for graphing of data over time, etc. There are some facilities for automatic monitoring of patients (e.g. EKG machines), which can be connected to alarm facilities at nurses stations, but these facilities are expensive, and don't allow the integration of arbitrary sensors, and they all require the use of cables, wires or tubes between the sensor and the patients. These cables, wires and tubes cause significant room clutter and are a trip and snag danger to the patient and the medical staff.

Some companies are beginning to commoditize the automation of patient monitoring by attaching wireless sensors to patients The patent data can be transmitted over an 802.11, other wireless, or wired network to a patient database. Such a system, however, requires securing of the links between the sensors and the patient database. This security must not only prevent eavesdropping by arbitrary attackers, but in order to comply with HIPAA, must enforce access control between legitimate members of the hospital community. There are no good solutions on the market for this problem, and traditional approaches, such as passwords, do not translate well to embedded devices such as sensors.

In yet another situation, patients using sensors at home face similar problems with securing data transmission to their doctors (or even configuring the monitoring devices to appropriately communicate data to their doctors). Some sensor devices use phone-based data transmission to handle both getting the data to the right place, and limiting access to the data in transit. However, the use of wireless sensors and the use of the internet or cellular phone networks to transmit such data is expected to increase as will the need to keep the data secure.

Turning to yet another problem, today, Emergency Operations Centers (EOC) communicate with the public largely using broadcast and telephony media. During an emergency EOC can use computer assisted dedicated switching systems to program specific messages for either the entire citizenry or a subset of those people who can be reached (for example, by specifying a location, type of building, or area of affect). The computer system in turn generates an automatic message that is played when a telephone is answered. The computer system then initiates calls to the targeted citizenry. The EOC can also communicate with the public by requesting that television and radio stations broadcast informational announcements. EOC commanders recognize that neither approach reaches all members of the public. In addition, the telephone calling system is easy for criminals to abuse.

It would be advantageous to provide a simpler way to create a secure credential infrastructure such as a PKI. It would also be advantageous to simplify the configuration (including the security aspects) of wireless access points (WAP) as well as simplifying the process of configuring a network even for wired networks. Furthermore, it would be advantageous to simplify the provisioning of sensors that provide data that needs to be secure. It would be still further advantageous to provide a secure means for providing public service notices.

DESCRIPTION OF THE PREFERRED EMBODIMENTS

One aspect of the embodiments disclosed herein is technology for creating a simple-to-use secure credential infrastructure. Such an infrastructure could be, for example, an "Instant PKI". That is, a PKI that is simple to establish, configure and use without diminishing the security provided by the PKI.

Another aspect is technology for automatically provisioning devices using a location-limited channel and of using this technology in exemplary systems such as for medical sensors and household alarms.

Still another aspect of the disclosed embodiments includes easily provisioned sensors that can securely send sensor data to a destination. Such sensors can be used in a wide variety of applications.

Yet another aspect of the disclosed embodiments includes secure situation notification devices that can be used to securely receive and present information directed to a specific receiver.

Figure 1:
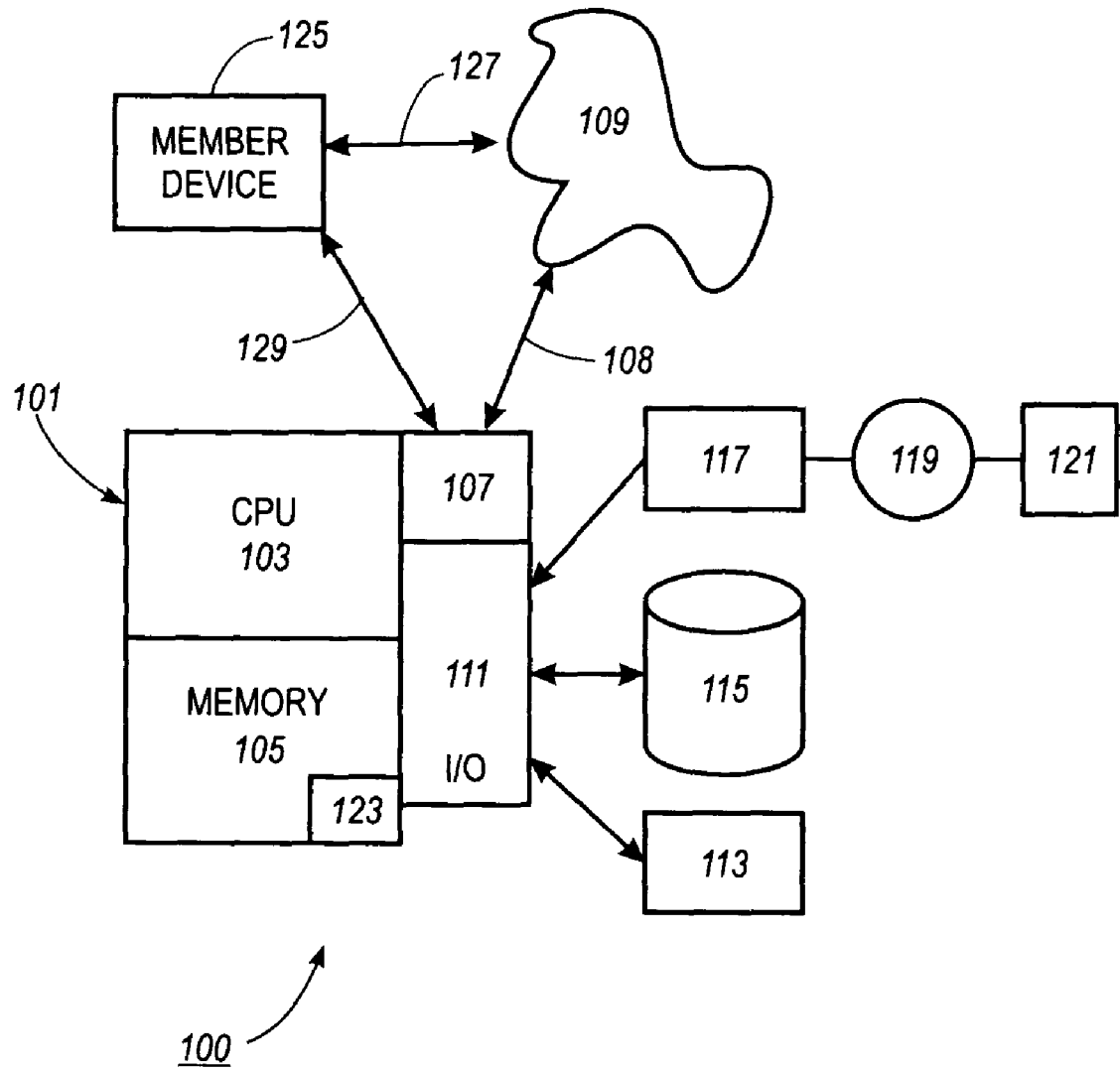
FIG. 1 illustrates a networked computer system in accordance with one embodiment.

FIG. 1 illustrates a networked computer system 100 that incorporates one embodiment of the invention. The networked computer system 100 includes a computer 101 that incorporates a CPU 103, a memory 105, and a network interface 107. The network interface 107 provides the computer 101 with access to a network 109 over a network connection 108. The computer 101 also includes an I/O interface 111 that can be connected to a user interface device(s) 113, a storage system 115, and a removable-media data device 117. The removable-media data device 117 can read a non-transitory computer readable media 119 that typically contains a program product 121. The storage system 115 (along with the removable media data device 117) and the computer readable media 119 comprise a file storage mechanism. The program product 121 on the computer readable media 119 is generally read into the memory 105 as a program 123. In addition, the program product 121, or updates to same, can be provided from the network as computer instruction signals embodied in a transmission medium (with or without a carrier wave upon which the signals are modulated or other data transporting technology—including light, radio, and electronic signaling) through the network interface 107. One skilled in the art will understand that a device in communication with the computer 101 can also be connected to the network 109 through the network interface 107 using the computer 101.

A member device 125 can also communicate over the network 109 over a network connection 127. The member device 125 can also communicate with the computer 101 over a preferred channel 129 through the network interface 107 or the I/O interface 111 (not shown).

One skilled in the art will understand that not all of the displayed features of the networked computer system 100 nor the computer 101 need to be present for all embodiments of the invention. Further, such a one will understand that the networked computer system 100 can be a networked appliance or device and need not include a general-purpose computer. The network connection 127, the network connection 108, and the preferred channel 129 can include both wired and wireless communication. In addition, such a one will understand that the user interface device(s) 113 can be virtual devices that instead of interfacing to the I/O interface 111, interface across the network interface 107.

Further, one skilled in the art will understand that a procedure can be a self-consistent sequence of computerized steps that lead to a desired result. These steps can be defined by one or more computer instructions. These steps can be performed by a computer executing the instructions that define the steps. Thus, the term "procedure" can refer (for example, but without limitation) to a sequence of instructions, a sequence of instructions organized within a programmed-procedure or programmed-function, or a sequence of instructions organized within programmed-processes executing in one or more computers. Such a procedure can also be implemented directly in circuitry that performs the steps. Further, computer-controlled methods can be performed by a computer executing an appropriate program(s), by special purpose hardware designed to perform the steps of the method, or any combination thereof. 100431 One embodiment is directed to the construction of a secure credential infrastructure. Such secure credential infrastructures include wired and wireless networks that use keys (for example, secret keys, or public-private key pairs) to encrypt information sent over a network such that the data representing the encrypted information only carries meaning to those computers that have the correct key, or a credential infrastructure that allows devices to use credentials to authenticate to other members, or to use credentials to authenticate to other members or service providers (for example, logging onto a Windows domain using a smart card that has a credential stored within it). This embodiment applies to secure credential infrastructures such as a public key infrastructure, to wireless networks (for example those using WEP encryption, or other wireless encryption standard), to wired networks, and to hybrid networks. One embodiment of the invention can be used to add target devices to a public key infrastructure (PKI) and thus, construct a PKI having member devices. Although much of the following is directed towards a secure credential infrastructure, one skilled in the art will understand that the inventive aspects apply as well to a PKI.

Figure 2:
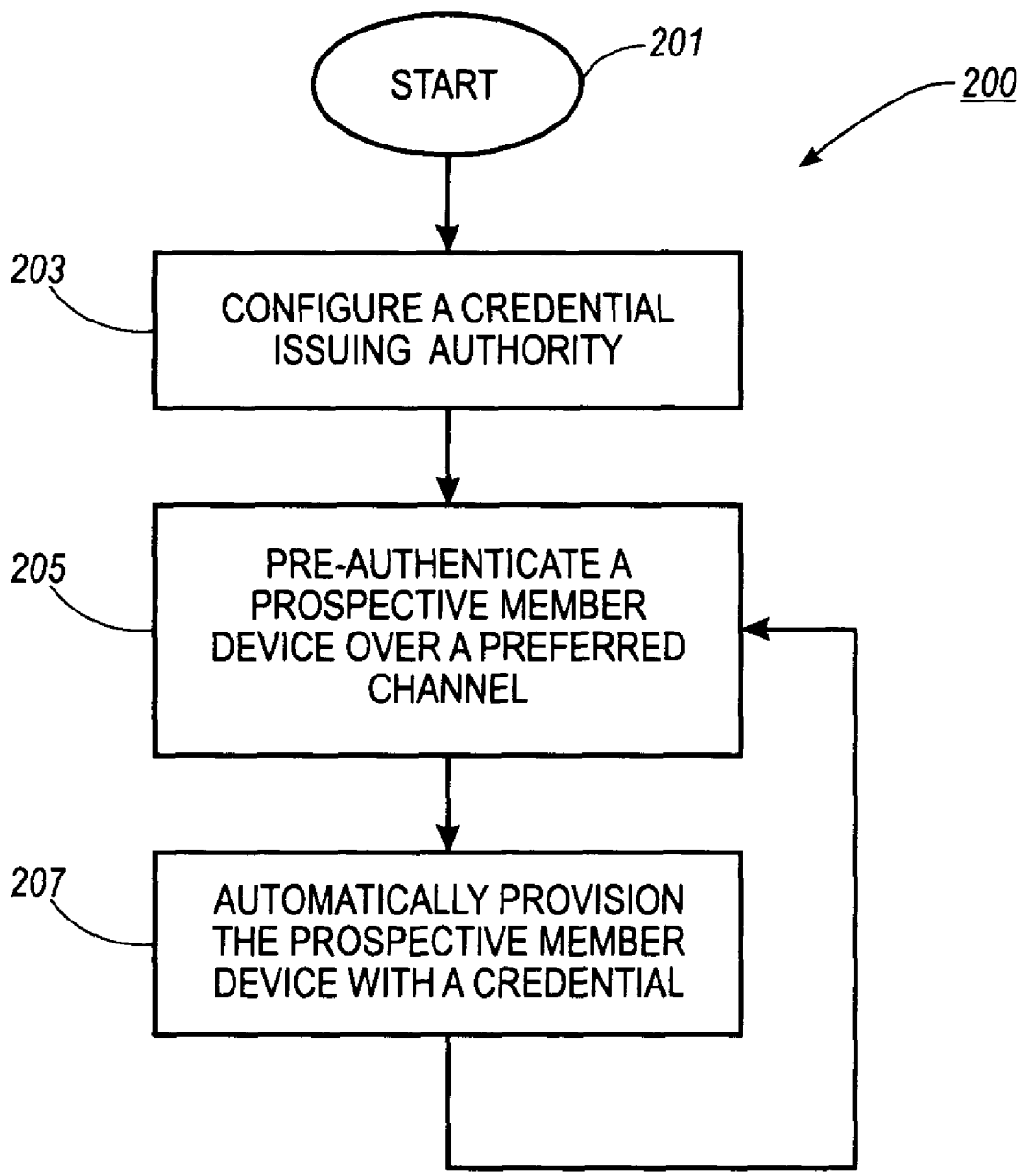
FIG. 2 illustrates a secure credential infrastructure construction process in accordance with one embodiment.

FIG. 2 illustrates a 'secure credential infrastructure construction' process 200 that is invoked when power is first applied to a credential issuing device, or when the credential issuing device is reset. The 'secure credential infrastructure construction' process 200 initiates at a 'start' terminal 201 and continues to a 'credential issuing authority configuration' procedure 203 that configures a credential issuing authority (for example a certification authority for a PKI) as is subsequently described with respect to FIG. 3.

Once the certification authority is configured, the 'secure credential infrastructure construction' process 200 continues to a 'prospective member device pre-authentication' procedure 205 that detects when a prospective member device is available to communicate to the credential issuing device over a preferred channel, optionally provides network configuration information to the prospective member device to enable it to communicate with the credential issuing device over some network other than the preferred channel, and pre-authenticates the prospective member device. The 'prospective member device pre-authentication' procedure 205 is subsequently described with respect to FIG. 4.

Once the prospective member device is pre-authenticated, an 'automatically provision prospective member device with credential' procedure 207 provisions the prospective member device by providing the prospective member device with a credential (in the PKI case, a public key certificate) for the prospective member device as well as the credential issuing device's public key certificate and any other information that is requested by the prospective member device, or automatically provided by the or enrollment station. Once provisioned, the prospective member device becomes a member device of the secure credential infrastructure. The 'automatically provision prospective member device with credential' procedure 207 is subsequently described with respect to FIG. 6.

The 'secure credential infrastructure construction' process 200 repeats back to the 'prospectibe member device pre-authentication' procedure 205 for each prospective member device be added to the secure credential infrastructure.

A credential can include a X.509 certificate, a WTLS certificate, a SPKI certificate, an attribute certificate, or any other association of a key or secret with trust, access, or identity.

Once the prospective member device is provisioned it becomes a member device and can use its credential as is known in the art. This includes using the credential to enable secure communications across a network, to use credential to provide access to devices, networks, services, containers, office space, or other device, area, or service that requires authentication and/or authorization or a credential to access.

Any device that performs the 'secure credential infrastructure construction' process 200 as well as any device that performs provisioning services for other secure networks is contemplated as a credential issuing device. Often, the credential issuing device includes a credential issuing authority (in the context of a PKI, a certification authority (CA)). One skilled in the art will understand that a public key infrastructure is but one instance of a secure credential infrastructure that includes a credential issuing authority (such as a certification authority) that provides a credential (such as a public key certificate) through a credential issuing device to the prospective member device. Possession of the credential by the prospective member device makes the device a member device of the secure credential infrastructure. Possession of the credential provides the member device with the ability to authenticate and/or authorize, or to access.

The preferred channel can be a location-limited channel or any other channel that has both a demonstrative identification property and an authenticity property.

The demonstrative identification property requires that identification be based on a physical context (for example but without limitation, "the printer in front of me," "all PDA's in the room," or "this device that I am touching"). The preferred channel uses communication technologies that have inherent physical limitations on their transmissions. Examples (but without limitation) of such technologies include visible or invisible electromagnetic radiation communication such as infrared communications, communications through a short run of wires, audio (both audible, and inaudible (for example ultrasonic)), communication by passing information from one device to another device using a physical computer-readable media (such as a removable media or drive (for example, a floppy disk, a removable disk, a USB storage device (such as a flash memory pen or disk drive) or other tangible data carrier)), physical electrical contact, near-field signaling across the body, and short range RF, as well as embodiments that require an operator to enter a code (other examples can be found in the discussion with respect to FIG. 8). The demonstrative identification property of the preferred channel means that human operators are aware of which devices are communicating with each other over the preferred channel and that the human operators can easily detect when an attack is being made on the preferred channel.

The authenticity property of the preferred channel means that it is impossible or difficult for an attacker to transmit over the preferred channel or tamper with messages sent over the preferred channel without detection by the legitimate parties to the communication.

The preferred channel does not require secrecy (that is, an attacker can monitor the transmissions on the preferred channel) so long as the attacker cannot transmit on the preferred channel without detection. Because of the location-limited nature of the preferred channel, it is difficult for an attacker to monitor the channel, let alone transmit on the channel without detection. Further, detection only requires that the human participants know the number of the participants (devices) who are communicating over the preferred channel.

As is subsequently described, the use of the preferred channel to pre-authenticate the participants' keys allows the administrator of the secure credential infrastructure to be assured that the keys are only provided to prospective member devices that have access to the preferred channel. Thus, establishing "trust" because the user of the prospective member device must have had physical access to the preferred channel (for example, when the user is an employee and has had access to the building where the preferred channel is located).

During the pre-authentication process, commitments (commitments are subsequently described) to each participant's public keys are exchanged over the preferred channel. Once the commitments are exchanged, the devices can perform a key exchange protocol or procedure and establish further secure communication using any method known in the art. To illustrate, once a key is received, it is verified by checking that the received key matches the commitment that was provided via the preferred channel. Once the keys are verified, well-known techniques can be used to commence communication using the keys (and in addition, in the case of a public key, also verifying that the other device holds the private key corresponding to the provided public key). Once the public keys are verified and the provider of the public key proves possession of the private key that corresponds to the public key, the credential issuing authority can provide a credential to the prospective member device for its use such that the prospective member device becomes an actual member device of the PKI.

A commitment to a piece of information X is a piece of information C that can be verified to match X. A commitment is "binding," when it is cryptographically difficult for an attacker, even knowing X and C, to produce a different piece of information Y that C will also match.

A commitment is "hiding" when it cryptographically difficult for an attacker knowing C to extract even partial information about X.

An example of a binding and hiding commitment to X can be H(X) where H can be a cryptographically secure hash function. One skilled in the art will understand from the context whether the commitment used needs to be binding, hiding, or both.

A commitment can be used to establish trust if it is received over a preferred channel or endowed with a digital signature from a party the recipient trusts. A trusted commitment allows the level of trust of a matching piece of information (possibly received over an untrusted channel, or unsigned) to be elevated to the same level of trust as the commitment.

Figure 3:
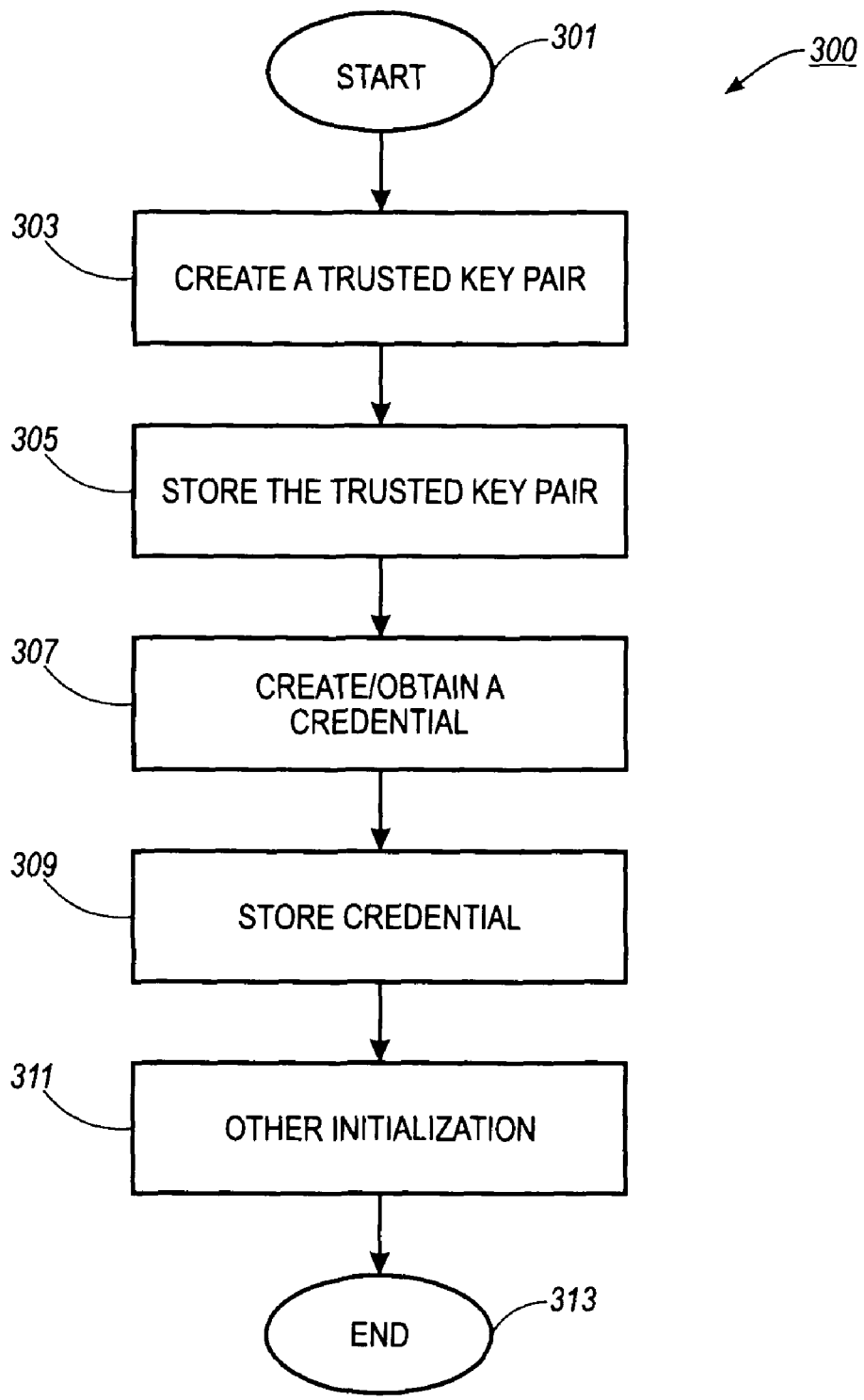
FIG. 3 illustrates a credential issuing authority configuration process in accordance with one embodiment.

FIG. 3 illustrates a 'credential issuing authority configuration' process 300 that can be used by the 'credential issuing authority configuration' procedure 203 of FIG. 2. This process can be used to initialize the credential issuing device so that it has a trusted credential. The 'credential issuing authority configuration' process 300 initiates at a 'start' terminal 301 and continues to a 'create trusted key pair' procedure 303 that generates public and private keys using well-known techniques. Once the trusted key pair is generated, a 'store trusted key pair' procedure 305 stores the trusted key pair on a storage device (for example, but without limitation, a disk, a cryptographic token, network device, network storage, memory card, etc.). Once the trusted key pair is generated, the 'credential issuing authority configuration' process 300 continues to a 'create issuing authority credential' procedure 307. One skilled in the art will understand that there are other types of credential systems other than certification systems that can be provisioned as described herein.

The 'create issuing authority credential' procedure 307 can create a self-signed credential (a "root" credential). The 'create issuing authority credential' procedure 307 can also access a parent certification authority to obtain a chained credential and to import the chained credential back to the credential issuing device. Once the credential is created or obtained, a 'store issuing authority credential' procedure 309 stores the credential in some available storage for subsequent use.

Other services or features can be initialized by an 'other initialization' procedure 311. These services and/or features can include directory services, generation of certificate revocation lists (CRLs) or credential status processing as well as other services. In addition, these services can include, for example, key-pair generation services, 802.11a/b/g provisioning services, network address provisioning services etc. The 'credential issuing authority configuration' process 300 completes through an 'end' terminal 313.

Figure 4:
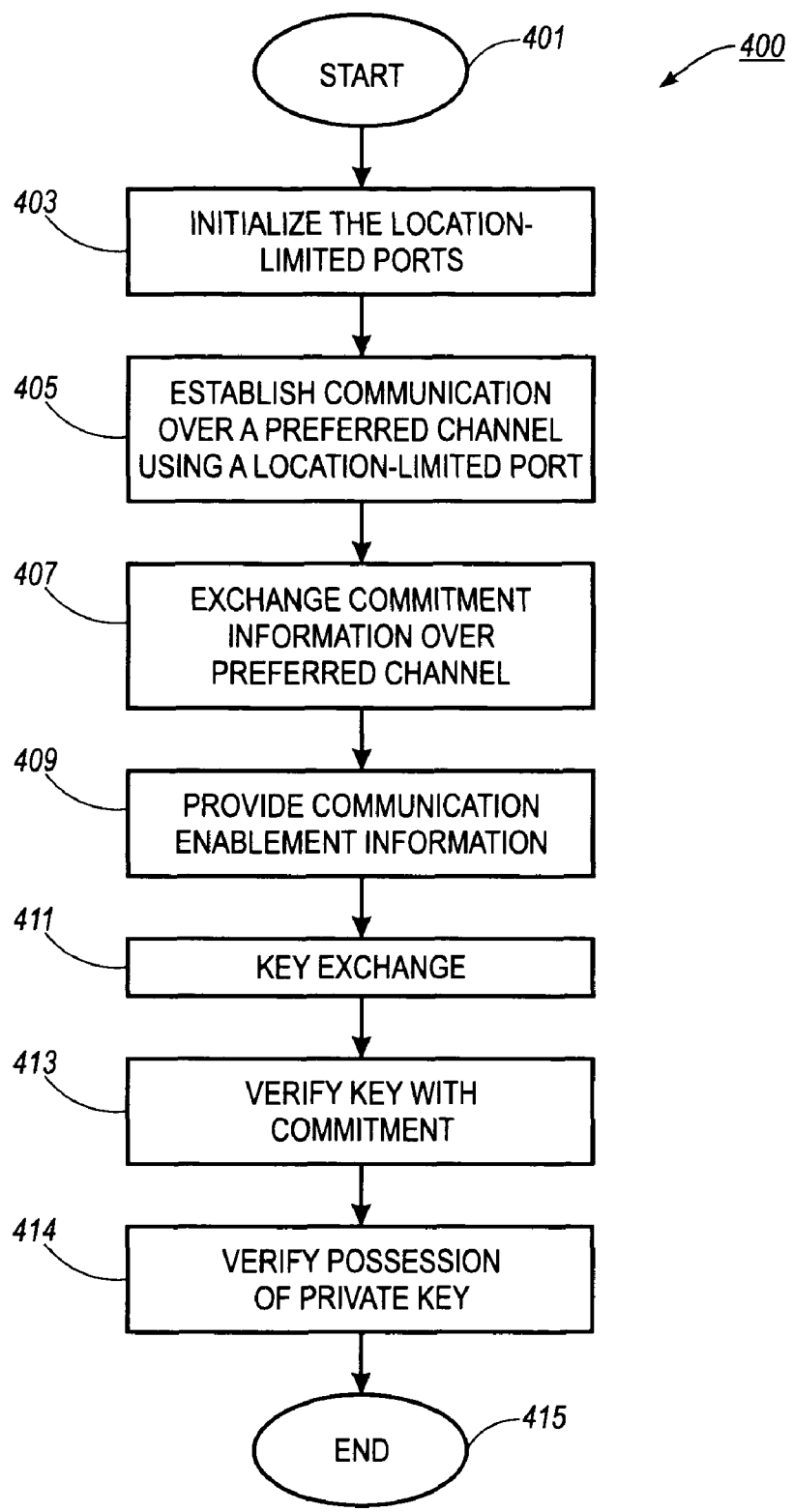
FIG. 4 illustrates a process that can be used by a credential issuing device to pre-authenticate a prospective member device over a preferred channel in accordance with one embodiment.

FIG. 4 illustrates a pre-authentication process for a credential issuing device 400 that can be used by the 'prospective member device pre-authentication' procedure 205 of FIG. 2.

The pre-authentication process for a credential issuing device 400 can be used to establish trust between the credential issuing device and the prospective member device such that the prospective member device can be provisioned with a credential and become a member device of the secure credential infrastructure.

The pre-authentication process for a credential issuing device 400 initiates at a 'start' terminal 401 and continues to an 'initialize location-limited ports' procedure 403 that activates one or more I/O ports of the credential issuing device that will be used to establish a preferred channel with the prospective member device.

Figure 8:
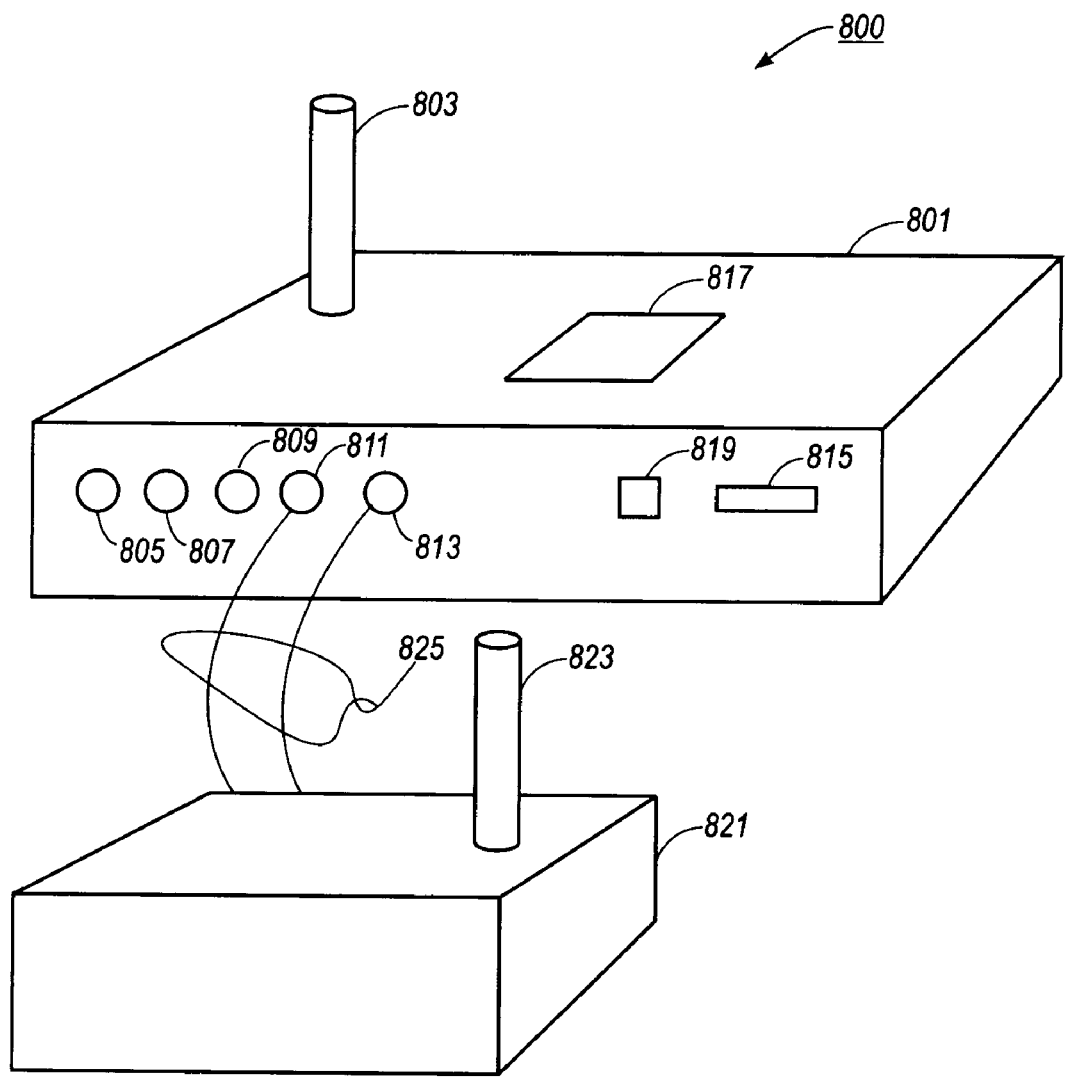
FIG. 8 illustrates one embodiment of a wireless access point secure credential infrastructure system.

A preferred channel can be established using any location-limited communication mechanism such as those described with respect to FIG. 8. Once the preferred channel ports are initialized, the pre-authentication process for a credential issuing device 400 continues to an 'establish communication over preferred channel' procedure 405 that establishes communication over the preferred channel between the credential issuing device and the prospective member device using one of the location limited ports initialized by the 'initialize location-limited ports' procedure 403. Once communication is established between the prospective member device and the credential issuing device (for example by aligning IR ports on the devices), the pre-authentication process for a credential issuing device 400 continues to an 'exchange commitment information' procedure 407 that generates a commitment for the public key. The commitment will be sent to the prospective member device over the preferred channel. The commitment can be a portion of the public key, the public key itself, an encoding of the public key, a mathematical function of the public key or other function of the key generated by any commitment technique. The credential issuing device also receives a commitment from the prospective member device for the key or secret that the prospective member device will send to the credential issuing device.

Next a 'provide communication enablement information' procedure 409 can provide the prospective member device with network configuration information required for the credential issuing device to communicate to the prospective member device over the desired communication media (as compared to the preferred channel). For example, where the credential issuing device is a WAP, it could specify the SSID and possibly a wireless channel selection and/or a WEP key; for a wired network, the credential issuing device could specify a specific MAC address and/or static IP address. One skilled in the art will understand that the 'provide communication enablement information' procedure 409 is optional in many embodiments and that the prospective member device can be pre-configured for network communication. However, one advantage of the 'provide communication enablement information' procedure 409 is that it simplifies the network configuration process for the prospective member device. For example, but without limitation, the credential issuing device can automatically assign a fixed network address to the prospective member device (as compared to a DHCP address), specify a SSID, specify a WEP key, a domain name, an IP address, a VPN address, gateway address, Bluetooth address, security settings, security policies, bit lengths, or other information needed to establish communication between the credential issuing device and the prospective member device over a channel other than the preferred channel. In addition, other information can be provided beyond just network configuration information. Furthermore, the communication enablement information can be used to bootstrap a secure communication channel that can be used to further provision the prospective member device, for example as is subsequently described with respect to FIG. 6. In addition, similar information can be provided during subsequent provisioning using a secure channel.

Once the commitments are exchanged, an 'key exchange' procedure 411 exchanges keys (for example using any key-exchange protocol known in the art) such that the credential issuing device and the prospective member device will be able to perform communication over a network that is not the preferred channel. The 'key exchange' procedure 411 need not use the preferred channel or an encrypted data path to exchange public keys. However, if secret keys are being exchanged secure communication are required (such as using the committed-to keys to establish secure communication over a non-preferred network; and using the established secure communication channel to negotiate exchange of a secret key). Furthermore, the preferred channel can be used with the 'key exchange' procedure 411 so long as any secret data is encrypted (and preferably using a protocol such as SSL). This can be useful where the preferred channel has sufficient bandwidth to timely carry the protocol.

Once the keys are exchanged, a 'verify keys with commitment' procedure 413 verifies that the received key matches the commitment (this can be done both by the credential issuing device and the prospective member device with the commitments and keys they have received respectively). For example, verifying that a received key matches a commitment can be performed by computing a cryptographic hash of the key and verifying that this hash is equal to the commitment. Once the public keys are verified by the commitment information, a 'verify possession of private key' procedure 414 establishes proof that the device providing the verified public key also has possession of the corresponding private key (for example using a key-pair validation mechanism that uses techniques well known in the art). Finally, the pre-authentication process for a credential issuing device 400 completes through an 'end' terminal 415.

In one embodiment of the invention, the actual key can be provided as the commitment. Then when keys are exchanged, verifying that the received key matches the previously received commitment can be done simply by verifying that they are equal.

Figure 5:
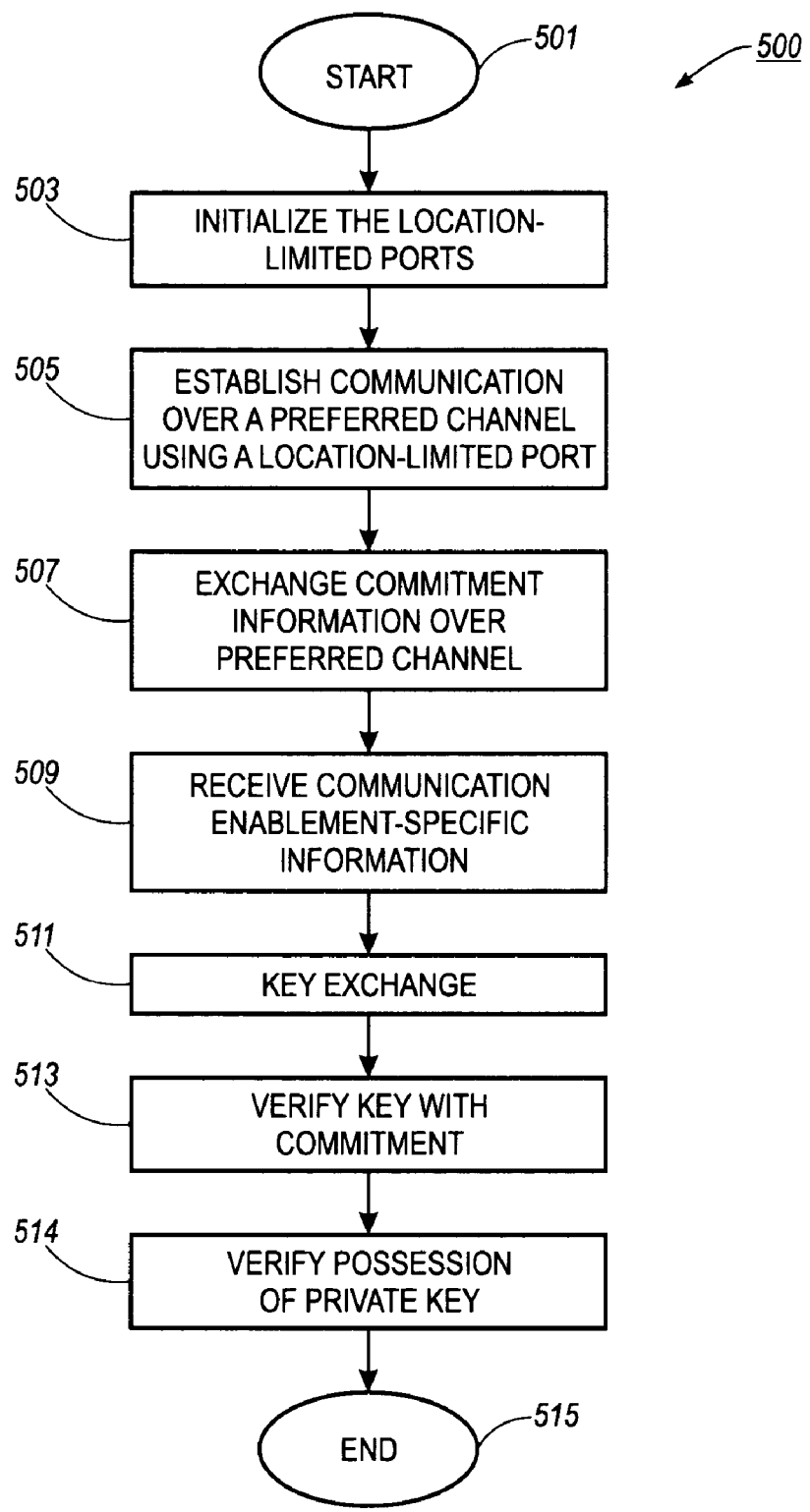
FIG. 5 illustrates a process that can be used by a prospective member device to pre-authenticate a credential issuing device over a preferred channel in accordance with one embodiment.

FIG. 5 illustrates a pre-authentication process for a prospective member device 500 that is very similar to the pre-authentication process for a credential issuing device 400 of FIG. 4. The pre-authentication process for a prospective member device 500 includes a 'start' terminal 501, an 'initialize location-limited ports' procedure 503, an 'establish communication over a preferred channel' procedure 505, an 'exchange commitment information' procedure 507, a 'receive communication enablement information' procedure 509, an 'key exchange' procedure 511, a 'verify keys with commitment' procedure 513, a 'verify possession of private key' procedure 514, and an 'end' terminal 515. These procedures are substantially the same as the corresponding procedure shown in FIG. 4 with the exception of the 'receive communication enablement information' procedure 509.

The 'receive communication enablement information' procedure 509 receives the information provided by the credential issuing device at the 'provide communication enablement information' procedure 409 and conditions the prospective member device so that it can communicate over one or more networks, or otherwise processes the communication enablement-specific information as appropriate.

With regards to the 'establish communication over preferred channel' procedure 405 and the 'establish communication over a preferred channel' procedure 505, there are at least two modes for establishing communication over the preferred channel. These modes differ in how the communication is established. In a first mode, the prospective member device can explicitly initiate the connection to the credential issuing device over the preferred channel and request a credential (either as part of an initial auto-configuration of the client, in request to stimuli from the environment—for example, detection of a new wireless network—, as a result of input from the user, or by an automated discovery process). This can be accomplished by having the prospective member device initiate the exchange of credentials with the designated the credential issuing device. One example of establishing a preferred channel is by aligning infrared or visible light ports of the prospective member device and the credential issuing device. Additional examples of connection examples are subsequently described with respect to FIG. 8.

Designation of the credential issuing device can be explicit (for example, "this device to which I have established an electrical connection", "this device I touch," "this device that is aligned with a specific IR port,") or implicit (for example, "any device that can receive audible signals issued from my device").

In the second mode, the communication over the preferred channel can be initiated by the credential issuing device in response to an action such as a user placing the prospective member device in a cradle attached to the credential issuing device by a serial port, or USB port or by having the prospective member device respond to a credential-granting token associated with the secure credential infrastructure. Using this approach, the prospective member device generally can be configured to be able to accept the pre-authentication requests from the credential issuing device. The prospective member device in this configuration, for example, can be executing an application that receives credentials and determines and processes the received credentials. In another example, the prospective member device can support a background program (for example, a UNIX daemon) that receives the credential and makes it available to other registered applications (with optional user confirmation or other feedback). Note that the cradle should not be a wireless cradle (that is, a cradle that wirelessly sends information to the credential issuing device) unless the communication between the cradle and the credential issuing device is secure.

A credential-granting token can include portable credential issuing devices (like a JAVA card), smart cards that can create credentials and directly provision prospective member devices. Other devices can, for example, serve as storage devices for accumulating and storing commitments between a group of prospective member devices that are to belong to a secure credential infrastructure. Finally, the credential issuing device can require identification of a key to enable the credential issuing function of the credential issuing device (for example, such a key can be a USB storage or biometric sensor that must be accessed prior to the credential issuing device provisioning a credential).

One skilled in the art will understand that the commitment to the key is transferred over the preferred channel because the preferred channel is assumed to be resistant to undetected active attacks and to thereby endow data transferred across it with the authenticity property. A channel does not need to be resistant to eavesdroppers to be used as a preferred channel because only public information (e.g. a public key, or a commitment to a public key) is sent over that channel; a pair of devices authenticating themselves to each other by sending such key or commitment information over the preferred channel are able to set up a secure communication with each other because they can demonstrate possession of the private keys corresponding to the public keys committed to or exchanged over the preferred channel (using any technique known in the art, such as a key exchange protocol like SSL/TLS). An eavesdropper that detects the commitment or keys sent across the preferred channel is not able to demonstrate possession of the corresponding private key, and therefore is unable to affect communication between the legitimate parties. Further, one skilled in the art will understand that the preferred channel can be a very low bandwidth channel as only needs to carry the key commitment (and possibly essential communication parameters for the non-preferred channel—such as a LAN, or Internet). The provisioning of the credential and other information to the prospective member device can be accomplished using the non-preferred channel(s).

Example protocols for exchanging commitments follow:

Pre-authentication for two keys, taking place over the preferred channel:

1. A→B: $addr_A$, $h(PK_A)$
2. B→A: $addr_B$, $h(PK_B)$

Authentication continues over a non-preferred (wireless) channel with any standard key exchange protocol to exchange $PK_A$ and $PK_B$ to establish secure communications, e.g.:

1. A→B: TLS CLIENT HELLO
2. . . . and so on.

The various symbols denote:

$addr_A$, $addr_B$: A's (resp. B's) address in wireless space, provided strictly for convenience;

$PK_A$, $PK_B$: the public key belonging to A (resp. B), either a long-lived key or an ephemeral key used only in this exchange;

$h(PK_A)$: a commitment to $PK_A$, e.g., a one-way hash of an encoding of the key.

Pre-authentication for one key, taking place over the preferred channel:

1. A→B: $addr_A$, $h(PK_A)$
2. B→A: $addr_B$, $h(S_B)$

Authentication continues over a non-preferred (wireless) channel with any standard key exchange protocol to exchange $PK_A$ and a secret, e.g.:

1. A→B: $PK_A$
2. B→A: $E_{PKA}(S_B)$

The various symbols denote:

$addr_A$, $addr_B$: A's (resp. B's) address in wireless space, provided strictly for convenience;

$PK_A$: the public key belonging to A either a long-lived key or an ephemeral key used only in this exchange;

$S_B$: a secret belonging to B;

$h(PK_A)$: a commitment to $PK_A$, e.g., a one-way hash of an encoding of the key.

Figure 6:
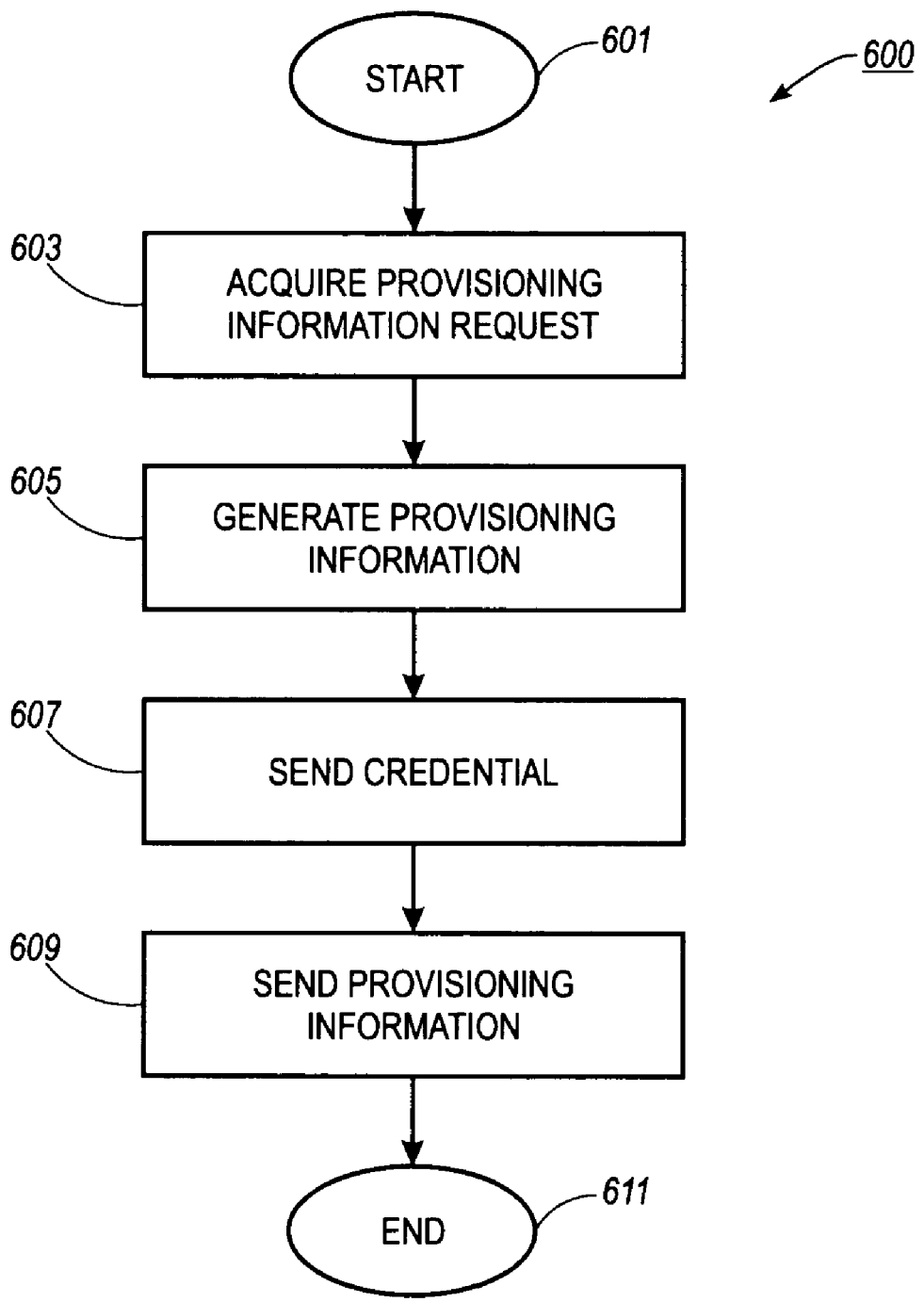
FIG. 6 illustrates an automatic prospective member device credential provisioning process in accordance with one embodiment.

$h(S_B)$: a commitment to $S_B$ $E_{PKA}(S_B)$: the encryption of $S_B$ Under $PK_A$ FIG. 6 illustrates an automatic prospective member device credential provisioning process 600 that can be used by the 'automatically provision prospective member device with credential' procedure 207 of FIG. 2. The automatic prospective member device credential provisioning process 600 provisions the prospective member device with the credential. It also sends the prospective member device other provisioning information (for example, information requested by the prospective member device or that is automatically provided by the credential issuing device.

The automatic prospective member device credential provisioning process 600 initiates at a 'start' terminal 601 and continues to an 'acquire provisioning information request' procedure 603. The 'acquire provisioning information request' procedure 603 can receive a request for provisioning information from the prospective member device. In addition, the 'acquire provisioning information request' procedure 603 can detect a condition that triggers the credential issuing device to provide pre-determined or user selected provisioning information. The request can include requests for information or services beyond that of just providing a credential.

Once the credential issuing device acquires the request, a 'generate provisioning information' procedure 605 generates a credential (such as one or more public key certificates) and any other requested provisioning information. The 'generate provisioning information' procedure 605 can include requesting authorization for the credential from a registration agent (for example from an RA in a PKI).

A 'send credential' procedure 607 causes the credential issuing device to send one or more credentials to the prospective member device. Once the prospective member device receives the credential, it becomes a member device of the secure credential infrastructure. Also, a 'send provisioning information' procedure 609 sends the provisioning information from the credential issuing device to the prospective member device.

The prospective member device can also request that it be provisioned with a key-pair generated by a credential issuing device or any other information that may be available. One skilled in the art will understand that some embodiments can send provisioning information that is not requested by the prospective member device (for example, application specific information).

Furthermore, the prospective member device can be provisioned with information that can be used by the prospective member device to establish a Virtual Private Network (VPN) with some other member device, security gateway, etc.

Figure 10:
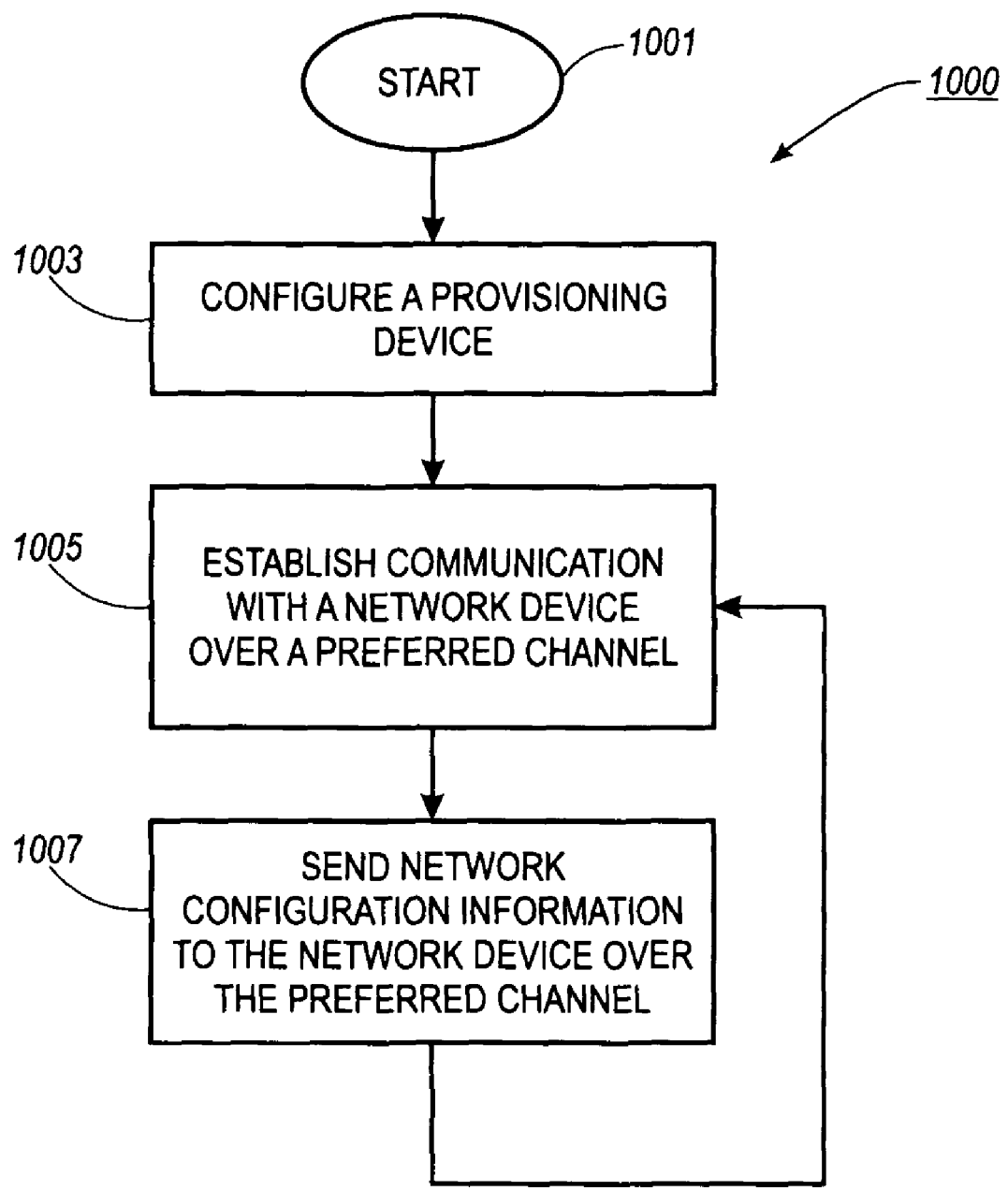
FIG. 10 illustrates an automatic network device configuration process in accordance with one embodiment.

One skilled in the art will understand that the 'automatically provision prospective member device with credential' procedure 207 in some embodiments will only provision the prospective member device with the credential, while other embodiments will provision the prospective member device with both the credential and other requested (or default) provisioning information (and in some embodiments may not provision a credential at all—see FIG. 10 and its discussion).

The provisioning information can be any information that can be used by the prospective member device. This information can include application specific information, site specific information, network specific information, or other information. This information can also include, for example but without limitation, information such as application-dependent information, device-specific assignment information (for example, in a hospital environment, the name of the patient, the case number, or other data-acquisition information required to capture data from the device or to cause the device to operate), database access information, cell phone provisioning information (such as the cell phone number), any kind of owner information, vehicle information, location information, information required to establish a secure communication link (for example VPN-related information), collaborative work space information, radio channel, any kind of application specific information, and information required to access a database. Thus, the term "provisioning" applies to the providing of a credential, as well as the providing of other information that can be used by a member device. In some embodiments, the provisioning information can be provided using multiple communication channels. In particular, the preferred channel can be used to send provisioning information to bootstrap subsequent communication (secure or not secured) over the preferred or non-preferred channel (for example, information necessary to establish temporary communication over a non-preferred channel). The two parties can then go on to exchange additional provisioning information over that non-preferred channel subsequent to the 'key exchange procedure' and 'key verification procedure' described above, which can be used to establish secure and authenticated communication between the parties over that non-preferred channel. This additional provisioning information can contain any of the provisioning information types described above, including communication enablement information sufficient to allow the new member device to communicate on another non-preferred network connection not used during the provisioning. In other embodiments, the preferred channel can be exclusively used to provision the prospective member device, possibly with the use of a key exchange protocol to additionally secure some of that communication. The more common embodiment will be where a first set of provisioning information is provided over the preferred channel, and other provisioning information is provided using a second (generally secure) communication channel.

Figure 7:
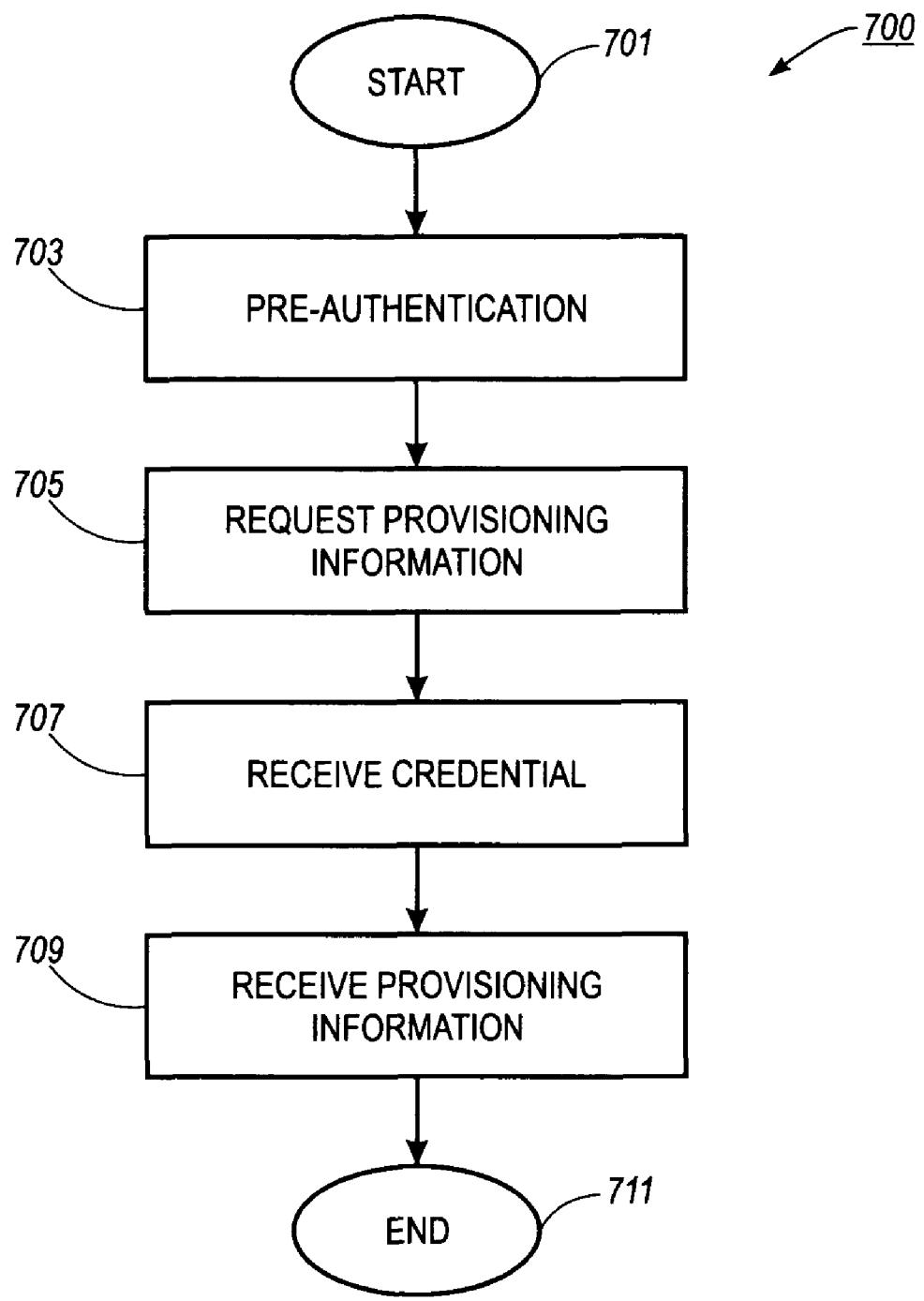
FIG. 7 illustrates one embodiment of the prospective member device provisioning process.

FIG. 7 illustrates a 'prospective member device-side provisioning' process 700 that can be used by the prospective member device to automatically receive a credential and other provisioning information from the credential issuing device. The 'prospective member device-side provisioning' process 700 initiates at a 'start' terminal 701 generally responsive to an event (for example, the detection of the potential for establishing a preferred channel, or in response to a user's action), and continues to a 'pre-authentication' procedure 703 (that invokes the pre-authentication process for a prospective member device 500 that has been previously described with respect to FIG. 5). Once the 'pre-authentication' procedure 703 completes, the prospective member device can communicate over a network. At a 'request provisioning information' procedure 705, the prospective member device sends a request for a credential and any other desired and available provisioning information. A 'receive credential' procedure 707 receives the credential and at a 'receive provisioning information' procedure 709 receives other requested provisioning information that was sent by the automatic prospective member device credential provisioning process 600. The received credential and possible other provisioning information can then be made available for use (whether by applications within the prospective member device, by readers of the prospective member device, or by other ways known in the art to use the credential). The 'prospective member device-side provisioning' process 700 completes through an 'end' terminal 711.

One skilled in the art will understand that some embodiments provision an IPSEC VPN instead of (or in addition to) 802.1X and EAP-TLS protocols on a wireless network (or for a wired network). Furthermore, other embodiments are envisioned that include a firewall and that automatically provision credentials to systems/users that allow the systems/users to communicate through the firewall. This can include allowing the system to connect over the VPN to the network protected by the firewall from the internet or wired or wireless LAN. Such a one will understand that some embodiments can be used to secure wireless LANs using techniques such a keyed hopping patterns, etc.

FIG. 8 illustrates a wireless access point secure credential infrastructure system 800 that uses a provisioning device 801 that is also configured as a wireless access point (WAP) for providing electronic signals through an antenna 803. WAPs are well known in the art and generally conform to 802.11(a), (b), or (g) although they can also conform to other standards currently in existence or yet to be developed. One skilled in the art will understand how to build a WAP. The provisioning device 801 is one embodiment of a credential issuing device and/or a provisioning device.

The provisioning device 801 can have additional functionality such as a switch, router, DSL or cable modem, firewall, VPN client or terminator, and a credential issuing authority. These capabilities are not shown in FIG. 8. The provisioning device 801 also has one or more ports that can be used to establish a preferred channel (for example, ports such as an infrared or visible communication port 805, a microphone 807, a speaker 809, an audio output 811, an audio input 813, a USB-A receptacle 815, a USB B receptacle 819, electrical contacts (not shown), and a near field detection area 817). The provisioning device 801 can establish a preferred channel with a prospective member device 821 using one of the ports in any number of ways. The preferred channels supported by the provisioning device 801 can include infrared, audible or inaudible audio (for example, sound and ultrasound), electrical representation of audio or other signals, information sent between the prospective member device 821 and the provisioning device 801 through a USB cable attached to the USB B receptacle 819, via a removable token that can be plugged into the USB-A receptacle 815 and passed to an appropriately equipped prospective member device, or by near field signaling by a human touching the near field detection area 817 on the provisioning device 801 while touching a detection area on the prospective member device 821. Furthermore, a preferred channel can include communication established using the telephone or cell phone switching system using signaling tones over a handset, or by direct connection to through a telephone jack.

Another possible port can be a camera used to capture an image of a computer screen that displays information (such as text, dataglyphs, or changing patterns). Another possible technology for the preferred channel can be short range radio frequency technology. Furthermore, the information can be provided to the prospective member device 821 and the provisioning device 801 using a keyboard, keypad, touch screen, etc. for having a user manually enter the information.

The prospective member device 821 includes an antenna 823, and one or more ports (not shown) that will enable communication across a preferred channel (in this case using audio connection cables 825 between the provisioning device 801) and the prospective member device 821.

The provisioning device 801 can be used to provision wireless networked devices by providing SSID codes and WEP keys, to provision wireless or wired network devices by providing network configuration information such as IP addresses, proxy information, domain information etc., to provision or provide application-specific information, or provision a credential.

For example, a computer, wireless access port (WAP), or other provisioning device having a preferred channel and that is configured to perform the 'secure credential infrastructure construction' process 200 can be used to construct a public key infrastructure.

When the credential issuing device is incorporated within a wireless access point (WAP) one embodiment of the invention can be used to provision network devices that access the WAP with network configuration information. This provisioning can be by adding the network device to the secure credential infrastructure such that the network device is a prospective member device. In addition, the credential issuing device can provide a key recognized by the WAP (for example a SSID and a key for used by a Wired Equivalent Privacy (WEP) capability in the WAP) to the network device over the preferred channel thus automating the error-prone and confusing entry of a long string of characters representing the key as is required by the current technology (some WAPs allow the use of a passphrase instead of directly providing the actual key, but the use of the passphrase reduces the WEP security—in addition, consider the difficulties of someone who is dyslexic when entering long arbitrary strings of characters)—further consider the consequence of naive users not understanding that the key is in hex base thus reducing the number of potential key combinations by limiting the text of the key to numeric characters.

One skilled in the art will understand that shared secrets as well as WEP keys can be provisioned (for example, any key shared by the infrastructure and one or more member devices). In particular, any "network password", or any type of symmetric key meant to either directly encrypt data for the wireless network, to authenticate a device to the wireless network, information required to establish a VPN on a wired or wireless network, and/or protect further key exchange.

Where the provisioning device 801 serves as a router, modem, or WAP, the provisioning device 801 can monitor the traffic passing through the provisioning device 801 to determine whether the traffic is from a member device (that is, a device that is authorized to use a secure channel) or from some other unauthorized device. Where the provisioning device 801 determines that the device is a member, packets sourced from the member device can be automatically routed through the secure channel while packets sourced from an unauthorized device are routed through an open channel.

One skilled in the art will understand how to apply these techniques to routers, bridges, hubs, firewalls, VPNs, and devices other than a WAP.

Figure 9:
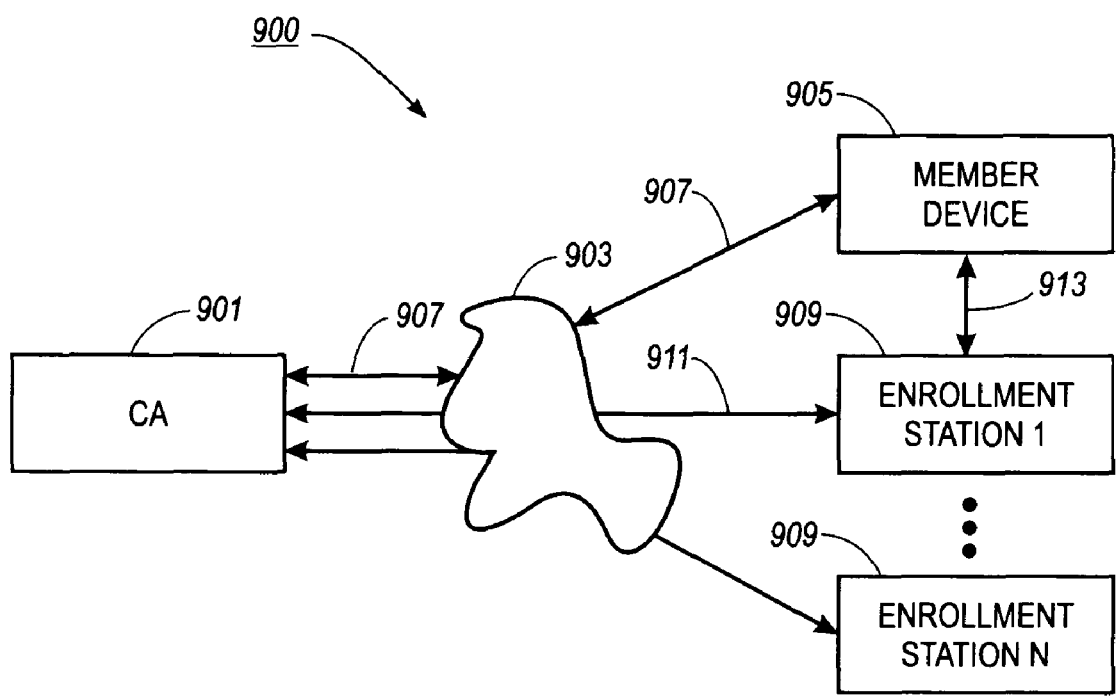
FIG. 9 illustrates an enrollment station based configuration system in accordance with one embodiment.

FIG. 9 illustrates an enrollment station based configuration 900 that allows a credential issuing device 901 (or certification authority) to access multiple enrollment stations (each having a location-limited channel) at different locations. This allows the location-limited channels to be deployed at multiple locations (such as at each remote office of a company). By deploying the enrollment stations at multiple locations, those who want to enroll a device in the secure credential infrastructure can do so simply by traveling to one of the enrollment stations. The use of the enrollment station can be one way to include a human in the certification process (such as a registration agent or other agent) to add additional information and authorize the enrollment of the prospective member device with the secure credential infrastructure. Another advantage of the use of the enrollment station is that it allows the credential issuing device 901 (providing the credential issuing authority service) to use off-the-shelf software that has no knowledge of pre-authentication or of the preferred channel.

A registration agent or other agent can also limit addition of prospective member devices (beyond the requirement that the prospective member device have access to the preferred channel as has been described throughout) by, for example but without limitation, using a special token (USB device, biometric sensor, etc.) to approve the preauthorization; using another device to approve the addition (for example, a requirement that the owner of the secure credential infrastructure (or authenticated user of the enrollment station) can be notified (and may need to provide approval) when a prospective member device is being pre-authenticated.

The credential issuing device 901 can communicate over a network 903 to a member device 905 over a network connection 907. In addition, the credential issuing device 901 can communicate to an enrollment station 909 over a secure network connection 911 (such as a VPN). The enrollment station 909 can enroll the member device 905 over a preferred channel 913 and communicate with the credential issuing device 901 over the secure network connection 911. The credential issuing device 901 and the enrollment station 909 can mutually authenticate each other using techniques known in the art as well as techniques described herein.

As was previously described, there exists a problem with simplifying the configuration of network devices. This problem can be addressed by another embodiment of the invention that is a network provisioning device. The network provisioning device has a preferred channel that can be used to provide a network device with network configuration information to enable the network device to communicate. Much of the detail of this function has been previously described.

FIG. 10 illustrates an automatic network device configuration process 1000 that can be used by the network provisioning device. The automatic network device configuration process 1000 initiates at a 'start' terminal 1001 at power on or reset and continues to a 'configure provisioning device' procedure 1003 that initializes the network provisioning device and allows a user or initialization system to specify the required network information. An 'establish communication with network device over a preferred channel' procedure 1005 establishes communication with the network device over a preferred channel in a similar manner as has been described (although in some embodiments with significantly less security). Once communication is achieved, a 'send network configuration information to network device' procedure 1007 sends the network configuration information to the network device. One skilled in that art will understand that a credential can also be provided if so desired as was previously described.

As was previously described, there exists a problem in the medical environment where cabled sensors are difficult to work around, but it is currently too difficult to provision wireless sensors to be sufficiently secure to protect the patient's privacy. However, having the capability to simply issue and administer credentials, as has been previously discussed, now enables a new solution to this problem.

Another embodiment of the invention can be applied to information management and distribution in environments where the data gathered by wireless sensors and where the data is private or legally protected. One example of such an environment is a hospital. Instead of the current labor intensive and cumbersome method of taking a patient's vital measurements—that is by requiring a human to take and record the measurements, using automated sensors to capture the patient's data and securely transmitting that data to a database or other repository. However, having wires attached to these sensors greatly adds to the hospital room clutter, and often annoy the patient, doctors, nurses and other hospital staff. Thus, wireless sensors would be desired. However, before this approach will succeed, the wireless sensors must be simple to setup and to secure such that no unauthorized individuals can access the patient data measured by the sensor.

As new devices (for example, sensors, data stations, etc.) are acquired by the hospital or medical practice, they can be configured at an enrollment station with a credential provided by a credential issuing authority as part of the hospital or practice security infrastructure. In addition, other configuration information (possibly entered by an operator) can be provided to the device to enable that device to operate in its usage environment (this information can include a commitment to the data server that the new device is to access, thus allowing the device to know that it is communicating with a legitimate data repository and preventing the use of rogue devices designed to gather patient data in an unauthorized fashion).

A particular sensor can then be associated (temporarily) with a particular patient by using a similar pre-authentication exchange with a bedside enrollment station associated with that patient, or with a configuration interface at a nurse's station or doctor's desk, which simply stores information about the public key of that device in the list of authorized devices for that patient. Communication between the sensor and the back-end hospital infrastructure, or remote data collection site is then secured using standard techniques (for example, IPsec, SSL), and data is associated with the appropriate patient by a combination of information provided by the device (that it received at configuration time), and the system's record of the devices associated with a particular patient.

In the case of remote monitoring, the hospital or practice firewall can be configured to allow incoming data connections from any of the devices with hospital/practice credentials (part of the instant PKI), along the lines of a self-configuring VPN.

Figure 11:
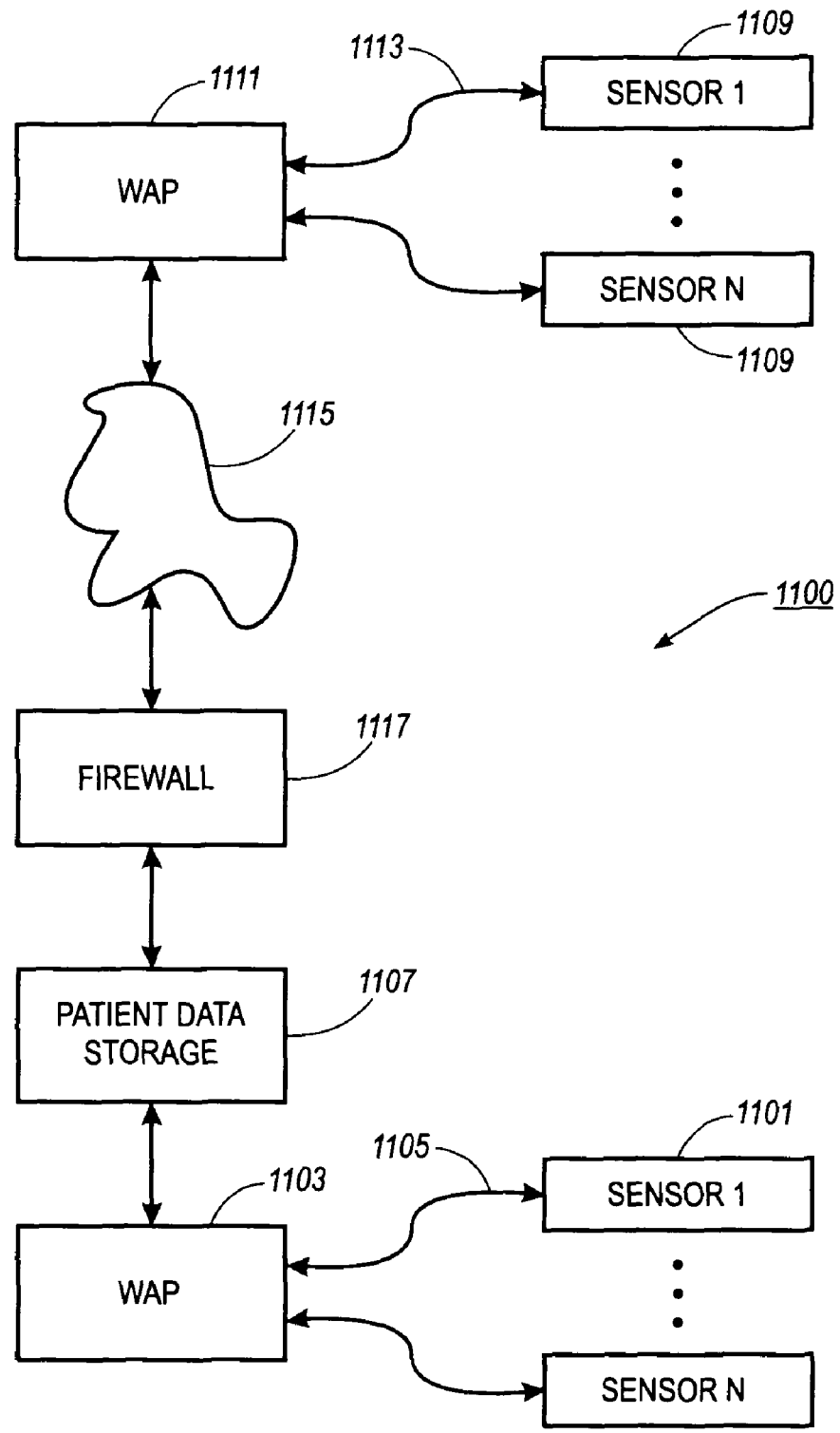
FIG. 11 illustrates a secure wireless sensor system deployed in a medical setting in accordance with one embodiment.

FIG. 11 illustrates a secure wireless sensor system 1100 showing the use of wireless sensors in the home and hospital settings. A patient is associated with a sensor 1101 that has been provisioned with a credential (as well as other data) as described above and provided with patent identification. The sensor 1101 gathers information related to the patient and securely sends that information to a patient data storage 1107 through the wireless access point 1103 over the wireless communication channel 1105 (for example, by establishing a secure communication channel using the provisioned credential). The sensors can securely communicate to any WAP in the medical facility as the patient moves thus maintaining continuous ability for the sensors to transmit information to the patient data storage 1107. Further, because wireless sensors are enabled by the some embodiments, additional sensors can be usefully attached to the patient. One such example is a sensor that recognizes the location of the patient such that the hospital administration can constantly know where a mobile patient is at any time. Such a sensor allows hospital staff to respond more quickly if other sensors indicate a problem with the patient (as well as being able to detect where a patient is when it time to administer medication). Other techniques can be used to track a patient by using triangulation methods based on the strength of wireless reception of multiple WAPs.

In addition, a nurse or other medical professional who has an appropriate credential can provision the sensor with patient specific information such as Patient identification, alarm limits, dosage schedules etc.

Sensors on a remote patient such as a remote sensor 1109 securely communicate to a wireless access point 1111 over a wireless communication channel 1113. The wireless access point 1111 sends the information through a network 1115 and a hospital firewall 1117 to the patient data storage 1107. The remote sensor 1109 can be provisioned at the hospital, at an enrollment station at the office of the patient's doctor, or otherwise. This approach to medical monitoring removes significant clutter in the patient's room, while still providing secure communication of the patient data.

One skilled in the art will understand that the wireless access point 1103 and the wireless access point 1111 can also be used as an enrollment station in communication with a credential issuing device at the hospital, can be used as a credential issuing device, and can also be used to provision the sensors with specific patient related data, such as patient data, limit data, alarm data, dosage data, interval data, access data, physician data, caregiver data, nurse data, insurance data and room assignment data.

One skilled in the art will understand that some embodiments can be applied to any sensor. In particular, some embodiments can be applied to elements of sensor networks for surveillance, home or office security, or other devices that need to be secure (including location and proximity sensors).

Furthermore, the sensor can sense and/or measure medical information, location information, proximity information, environmental information (such as exposure to particle radiation, chemical vapors, sound levels, smoke levels, environmental heat, altitude, wind speed, vibration, proximity to motion, humidity, and biological agents), as well as sensors within a vehicle or group of vehicles (such as vehicle speed, vehicle orientation, status of vehicle sub-components (such as airfoils, engine or motor measurements, brakes, etc.), or robots). Further sensors can be used to recognize images of locations, objects, people, and targets as well as recognizing characteristic noises. Such sensors can also have activation components that are controlled by data within the provisioning information (such as dosage data, interval data, activation data, etc.).

Another problem solved by some embodiments is that of providing secure communications between an emergency operation center (EOC) and the residents at potential risk from an emergency. As previously described, there exists a problem with current means for providing citizens with emergency warnings. These problems include the difficulty of reaching only a portion of the citizen base, and the difficulty in making sure that the warning system is secure such that unsavory characters cannot use the system to annoy or harass citizens.

Having the capability to simply issue and administer credentials, as has been previously discussed, now allows a new solution to this problem.

Figure 12:
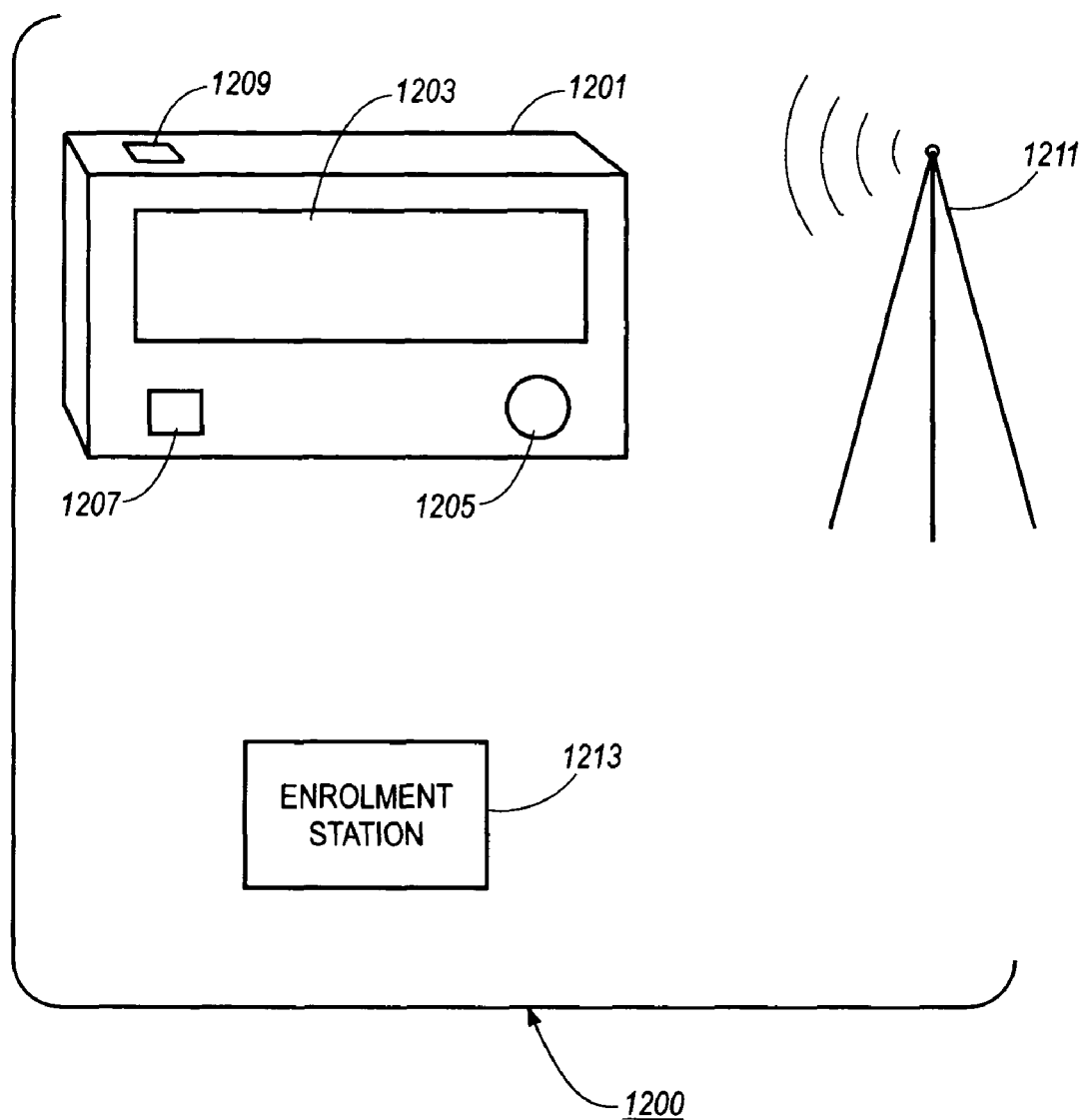
FIG. 12 illustrates one embodiment of a secure community alert system.

FIG. 12 illustrates one embodiment of a secure community alert system 1200. Each person covered by the secure community alert system 1200 receives a resident alert device 1201 (or other situation notification device) for insertion in the resident's domicile. The resident alert device 1201 includes a display portion 1203 that serves as a means of providing information to those in the domicile. It also includes an audible speaker 1205 for alerting those in the domicile and a warning light/disable switch 1207 for providing a visual alert, a means for silencing the audible speaker 1205, and means to respond to messages displayed on the display portion 1203. The resident alert device 1201 also includes an enrollment port 1209 that can enable a preferred channel as previously described (however, the enrollment port 1209 can also be a telephone or Ethernet jack such that the resident alert device 1201 can be provisioned from a known telephone number or internet address). The resident alert device 1201 can receive alarm information (or general subject matter information) from a transmission mechanism 1211 such as by an emergency radio or television station or other wireless means (for example by use of the cellular phone system), by use of the wired telephone system, by use of the Internet, or any other data communication mechanism.

Some of the embodiments of the resident alert device 1201 can have additional options for the hearing or visually impaired, those who cannot read, etc.

The resident alert device 1201 can be provisioned by an enrollment station 1213. Provisioning can be accomplished at the time the resident alert device 1201 is provided to the resident, by providing the device un-provisioned such that the resident provisions the device at home by connecting the device to the telephone network. People without security expertise can now provision the resident alert device 1201 because provisioning is now a simple procedure.

Another aspect that can be provided by some embodiments of the resident alert device 1201 is that of a forwarding service. That is, once the alert is received by the resident alert device 1201, the alert can be forwarded to an e-mail address, text messaging system, or voice telephone number.

The functions of the resident alert device 1201 can be incorporated into other home and office electronic devices such as a computer, a television, a radio, a telephone, a push to talk device, a pager, a clock, a thermostat, a network appliance, or a home appliance.

During an emergency it is critical that the EOC can communicate with that device in a way that provides certain guarantees.

For the citizen it is necessary to know that the communication is a genuine alert from the EOC and not, say, some criminal who is attempting to get the home owners to leave their house in a hurry and potentially leave the house vulnerable to theft.

For the EOC it is important to be able to specify the devices and be certain that they are communicating with the intended devices and only the intended devices. This requirement would be necessary in a flood emergency for example, where evacuation instructions would need to be issued to people in stages of danger and direct them to different places, via different routes to avoid congestion en route and at the evacuation sites.

One skilled in the art will understand that the network transmits information (such as the previously described data as well as data that defines a computer program). Generally, the information is embodied within a carrier-wave. The term "carrier-wave" includes electromagnetic signals, visible or invisible light pulses, signals on a data bus, or signals transmitted over any wire, wireless, or optical fiber technology that allows information to be transmitted over a network. Programs and data are commonly read from tangible physical media (such as a compact, floppy, or magnetic disk).

In addition, the flowcharts provided herein are for illustrative purposes and are used to teach one embodiment of the invention. Other flowcharts that incorporate the underlying ideas (or modifications thereof) are to be considered as equivalent.

One skilled in the art will understand that embodiments of the invention vastly simplify the creation, management, and maintenance of secure credential infrastructure. Thus, a PKI can be cheaply and efficiently created and administered. Furthermore, the characteristics of some embodiments now enable the use of secure credential infrastructure in applications and environments where the expense and overhead related to traditional secure credential infrastructure were prohibitive.

From the foregoing, it will be appreciated that embodiments of the invention have (without limitation) one or more of the following advantages:

1) ability to quickly and simply create, maintain, and manage secure credential infrastructure by non-security exports;

2) dramatically improved security available to the public because of the decrease in cost and effort in creating a secure credential infrastructure now enables the computer layperson to keep their communications secure;

3) enables the use of wireless sensors that provide sensitive personal data about the person without fear of the information be intercepted or of violating privacy statutes;

4) enables the use of alarm systems (such as neighborhood alert systems) that are completely secure from being misused by somebody outside of the alarm system;

5) enables simple setup of secure wireless access points;

6) enables simple provisioning of network devices (either with credentials, with network-specific information, application-specific information, or combination of these; and 7) enables the ability to join a PKI without requiring onerous trust verification processes.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A computer controlled method comprising:
    providing a security credential to a resident alert device, wherein the resident alert device is inserted in a domicile for a resident covered by a secure community alert system to receive information from an emergency operation center that transmits a set of instructions in an emergency;
    establishing communication between the resident alert device and a provisioning device over a preferred channel, the resident alert device configured to send the security credential to the provisioning device over the preferred channel and to receive a commitment from the provisioning device over the preferred channel;
    receiving from the provisioning device over the preferred channel at least one of provisioning information or additional application-specific information, site-specific information, network-specific information, or other information that can be used by the resident alert device, wherein the provisioning information includes a credential and wherein the credential facilitates the resident alert device to become a member of a secure credential infrastructure; and
    automatically configuring the resident alert device for receiving information over a secure communication channel responsive to the provisioning information.

2. The computer controlled method of claim 1, further comprising transmitting information from the resident alert device over the secure communication channel.

3. The computer controlled method of claim 1, wherein the preferred channel comprises a single location-limited channel capable of communicating both from the wireless sensor to the provisioning device and from the provisioning device to the wireless sensor.

4. The computer controlled method of claim 1, wherein the preferred channel comprises two separate channels, including a first location-limited channel capable of communicating from the wireless sensor to the provisioning device and a second location-limited channel capable of communicating from the provisioning device to the wireless sensor.

5. The computer controlled method of claim 1, further comprising receiving the at least one of the provisioning information or additional application-specific information from the provisioning device over at least one of: a telephone network, or the Internet.

6. The computer controlled method of claim 1, wherein receiving information over the secure communication channel further comprises receiving information from at least one of: emergency radio station, television station, cellular phone system, wired telephone system, or the Internet.

7. The computer controlled method of claim 1, further comprising identifying an intended resident alert device at an emergency operation center, and transmitting information from the emergency operation center to the intended resident alert device.

8. The computer controlled method of claim 1, wherein each instruction corresponds to a different set of people in the emergency, and wherein the information received by the resident alert device from the emergency operation center includes the instruction corresponding to the resident.

9. The computer controlled method of claim 8, wherein the instructions include evacuation instructions, and wherein each evacuation instruction directs the corresponding set of people to a different place.

10. The computer controlled method of claim 1, wherein the emergency includes a flood emergency.

11. A non-transitory computer-readable storage medium storing instructions that when executed by a computer cause the computer to perform a method comprising steps of:
    providing a security credential to a resident alert device, wherein the resident alert device is inserted in a domicile for a resident covered by a secure community alert system to receive information from an emergency operation center that transmits a set of instructions in an emergency;
    establishing communication between the resident alert device and a provisioning device over a preferred channel, the resident alert device configured to send the security credential to the provisioning device over the preferred channel and to receive a commitment from the provisioning device over the preferred channel;
    receiving from the provisioning device over the preferred channel at least one of provisioning information or additional application-specific information, site-specific information, network-specific information, or other information that can be used by the resident alert device, wherein the provisioning information includes a credential and wherein the credential facilitates the resident alert device to become a member of a secure credential infrastructure; and
    automatically configuring the resident alert device for receiving information over a secure communication channel responsive to said provisioning information.

12. The non-transitory computer-readable storage medium of claim 11, further comprising transmitting information from the resident alert device over the secure communication channel.

13. The non-transitory computer-readable storage medium of claim 11, wherein the preferred channel comprises a single location-limited channel capable of communicating both from the wireless sensor to the provisioning device and from the provisioning device to the wireless sensor.

14. The non-transitory computer-readable storage medium of claim 11, wherein the preferred channel comprises two separate channels, including a first location-limited channel capable of communicating from the wireless sensor to the provisioning device and a second location-limited channel capable of communicating from the provisioning device to the wireless sensor.

15. An apparatus comprising:
    a mechanism configured to provide a security credential to a resident alert device, wherein the resident alert device is inserted in a domicile for a resident covered by a secure community alert system to receive information from an emergency operation center that transmits a set of instructions in an emergency;
    at least one port configured to establish a preferred channel;
    a preferred channel communication mechanism configured to establish communication with a provisioning device over the preferred channel, the preferred channel communication mechanism further configured to send the security credential to the provisioning device over the preferred channel and to receive a commitment from the provisioning device over the preferred channel;

a receiver mechanism configured to receive from the provisioning device over the preferred channel at least one of provisioning information or additional application-specific information, site-specific information, network-specific information, or other information that can be used by the resident alert device, wherein the provisioning information includes a credential and wherein the credential facilitates the resident alert device to become a member of a secure credential infrastructure; and an automatic configuration mechanism to enable the resident alert device to receive information over a secure communication channel established responsive to said provisioning information.

16. The apparatus of claim 15, further comprising a transmission mechanism configured to transmit information from the resident alert device over the secure communication channel.

17. The apparatus of claim 15, wherein the information received by the resident alert device is information from an emergency operation center.

18. The apparatus of claim 15, wherein the preferred channel comprises a single location-limited channel capable of communicating both from the wireless sensor to the provisioning device and from the provisioning device to the wireless sensor.

19. The apparatus of claim 15, wherein the preferred channel comprises two separate channels, including a first location-limited channel capable of communicating from the wireless sensor to the provisioning device and a second location-limited channel capable of communicating from the provisioning device to the wireless sensor.

* * * * *